(12) United States Patent
DeJohn et al.

(10) Patent No.: US 12,023,666 B2
(45) Date of Patent: Jul. 2, 2024

(54) METHODS AND SYSTEMS FOR AUTOMATED SAMPLE PROCESSING

(71) Applicant: Biomeme, Inc., Philadelphia, PA (US)

(72) Inventors: Marc DeJohn, Philadelphia, PA (US); Christopher Cox, Elkins Park, PA (US)

(73) Assignee: Biomeme, Inc., Philadephia, PA (US)

( * ) Notice: Subject to any disclaimer, the term of this patent is extended or adjusted under 35 U.S.C. 154(b) by 24 days.

(21) Appl. No.: 16/817,733

(22) Filed: Mar. 13, 2020

(65) Prior Publication Data
US 2020/0276582 A1 Sep. 3, 2020

Related U.S. Application Data

(63) Continuation of application No. PCT/US2018/051228, filed on Sep. 14, 2018.
(Continued)

(51) Int. Cl.
| | | |
|---|---|---|
| *C12Q 1/686* | (2018.01) | |
| *B01L 3/00* | (2006.01) | |
| *B01L 7/00* | (2006.01) | |

(52) U.S. Cl.
CPC .......... *B01L 3/502715* (2013.01); *B01L 7/52* (2013.01); *C12Q 1/686* (2013.01); *B01L 2200/10* (2013.01);
(Continued)

(58) Field of Classification Search
CPC ..... B01L 2300/0681; B01L 2400/0487; B01L 3/502715; B01L 7/52; B01L 2200/10; B01L 2200/16; B01L 2300/0867; B01L 3/5027; B01L 3/527; C12Q 1/68; C12Q 2565/629; C12Q 1/686
See application file for complete search history.

(56) References Cited

U.S. PATENT DOCUMENTS

| | | | |
|---|---|---|---|
| 3,757,780 A | 9/1973 | Ishikawa | |
| 5,151,192 A | 9/1992 | Matkovich et al. | |

(Continued)

FOREIGN PATENT DOCUMENTS

| | | | |
|---|---|---|---|
| CN | 1680574 A | 10/2005 | |
| CN | 1687391 A | 10/2005 | |

(Continued)

OTHER PUBLICATIONS

European search report and search opinion dated Jun. 22, 2017 for EP Application No. EP14859198.5.
(Continued)

*Primary Examiner* — Young J Kim
(74) *Attorney, Agent, or Firm* — Wilson Sonsini Goodrich & Rosati

(57) ABSTRACT

The present disclosure provides devices, systems, methods and kits for processing a sample. In some cases, a sample is processed in preparation for an assay (e.g., polymerase chain reaction and immunofluorescence-based target detection) by an analytic device. In some cases, the processing is automated. In some cases, the processing is substantially automated. The systems provided herein can comprise a cartridge (e.g., one-time use) and a dock (e.g., re-useable) for receiving the cartridge. In some cases, the devices and systems provided herein are portable.

19 Claims, 19 Drawing Sheets

Related U.S. Application Data

(60) Provisional application No. 62/688,861, filed on Jun. 22, 2018, provisional application No. 62/559,173, filed on Sep. 15, 2017.

(52) U.S. Cl.
CPC .................. *B01L 2300/0681* (2013.01); *B01L 2300/0816* (2013.01); *B01L 2300/0867* (2013.01); *B01L 2300/0874* (2013.01); *B01L 2400/0487* (2013.01); *B01L 2400/0661* (2013.01)

(56) References Cited

U.S. PATENT DOCUMENTS

| | | |
|---|---|---|
| 5,529,391 A | 6/1996 | Kindman et al. |
| 5,616,301 A | 4/1997 | Moser et al. |
| 5,626,567 A | 5/1997 | Gmeiner |
| 5,849,488 A | 12/1998 | Alatossava et al. |
| 6,274,371 B1 | 8/2001 | Colpan |
| 6,746,864 B1 | 6/2004 | McNeil et al. |
| 7,167,755 B2 | 1/2007 | Seeberger et al. |
| 7,759,112 B2 | 7/2010 | Belgrader |
| 7,943,348 B2 | 5/2011 | Cho et al. |
| 8,361,316 B2 | 1/2013 | Siddiqi |
| 8,454,892 B1 | 6/2013 | Rychwalski et al. |
| 8,633,032 B2 | 1/2014 | Akashi et al. |
| 8,940,524 B2 | 1/2015 | Cobb |
| 9,314,570 B2 | 4/2016 | Kim |
| 9,535,676 B1 | 1/2017 | Forehand et al. |
| 9,575,655 B2 | 2/2017 | Rytivaara |
| 9,579,655 B2 | 2/2017 | DeJohn et al. |
| 9,618,139 B2 | 4/2017 | Handique |
| 9,926,553 B2 | 3/2018 | De John et al. |
| 10,036,058 B2 | 7/2018 | Baumgartner et al. |
| 10,457,983 B2 | 10/2019 | Dejohn et al. |
| 11,299,728 B2 | 4/2022 | Dejohn et al. |
| 2001/0003652 A1 | 6/2001 | Freeman |
| 2001/0007062 A1 | 7/2001 | Dumaresq-Lucas et al. |
| 2001/0012612 A1 | 8/2001 | Petersen et al. |
| 2002/0150907 A1 | 10/2002 | Fomovskaia et al. |
| 2004/0126279 A1 | 7/2004 | Renzi et al. |
| 2004/0208796 A1 | 10/2004 | Chiga |
| 2005/0033196 A1 | 2/2005 | Alroy |
| 2006/0001870 A1 | 1/2006 | Voigt et al. |
| 2006/0213827 A1 | 9/2006 | Nozaki |
| 2006/0216206 A1 | 9/2006 | Hudson et al. |
| 2006/0222567 A1 | 10/2006 | Kloepfer et al. |
| 2007/0035732 A1 | 2/2007 | Marsche et al. |
| 2007/0122809 A1 | 5/2007 | Stevenson et al. |
| 2008/0145848 A1 | 6/2008 | Stephan et al. |
| 2008/0145858 A1 | 6/2008 | Kim et al. |
| 2008/0254532 A1 | 10/2008 | Chang et al. |
| 2009/0111193 A1 | 4/2009 | Cooney et al. |
| 2009/0142333 A1 | 6/2009 | Knopf et al. |
| 2009/0143233 A1 | 6/2009 | Knight et al. |
| 2010/0177950 A1 | 7/2010 | Donovan et al. |
| 2010/0204462 A1 | 8/2010 | Walter et al. |
| 2011/0057117 A1 | 3/2011 | Fawcett et al. |
| 2011/0076735 A1 | 3/2011 | Jovanovich et al. |
| 2011/0201099 A1 | 8/2011 | Anderson et al. |
| 2011/0290647 A1 | 12/2011 | Feiglin |
| 2012/0077259 A1 | 3/2012 | Cobb |
| 2012/0220024 A1 | 8/2012 | Cobb |
| 2012/0288892 A1 | 11/2012 | Maiyuran et al. |
| 2012/0288897 A1 | 11/2012 | Ching et al. |
| 2013/0028814 A1 | 1/2013 | Numai |
| 2013/0078619 A1 | 3/2013 | Cooney et al. |
| 2013/0115607 A1 | 5/2013 | Nielsen et al. |
| 2013/0230845 A1 | 9/2013 | Egan et al. |
| 2014/0008311 A1 | 1/2014 | Weston et al. |
| 2014/0206412 A1 | 7/2014 | DeJohn et al. |
| 2015/0024436 A1 | 1/2015 | Eberhart et al. |
| 2015/0111287 A1 | 4/2015 | Rawle |
| 2015/0126724 A1 | 5/2015 | De John et al. |
| 2016/0041095 A1 | 2/2016 | Rothberg et al. |
| 2016/0069921 A1 | 3/2016 | Holmes et al. |
| 2016/0115520 A1 | 4/2016 | Krishnamurthy |
| 2016/0155120 A1 | 6/2016 | Hurry |
| 2016/0169924 A1 | 6/2016 | Torgerson et al. |
| 2016/0230210 A1 | 8/2016 | Chen et al. |
| 2016/0231171 A1 | 8/2016 | Assefa et al. |
| 2016/0265040 A1 | 9/2016 | Baumgartner et al. |
| 2017/0068533 A1 | 3/2017 | Kiaie et al. |
| 2017/0183713 A1 | 6/2017 | DeJohn et al. |
| 2017/0327867 A1* | 11/2017 | Dohale ................ B01L 3/5021 |
| 2017/0333894 A1* | 11/2017 | Khalid ................ H01J 37/3233 |
| 2018/0105810 A1 | 4/2018 | Dejohn et al. |
| 2020/0080133 A1 | 3/2020 | DeJohn et al. |
| 2020/0276582 A1 | 9/2020 | DeJohn et al. |
| 2020/0376494 A1 | 12/2020 | DeJohn et al. |
| 2022/0074847 A1 | 3/2022 | Eisenhower et al. |
| 2022/0186325 A1 | 6/2022 | Dejohn et al. |
| 2022/0315916 A1 | 10/2022 | DeJohn et al. |

FOREIGN PATENT DOCUMENTS

| | | |
|---|---|---|
| CN | 101722071 A | 6/2010 |
| CN | 101868721 A | 10/2010 |
| CN | 102348985 A | 2/2012 |
| CN | 102472695 A | 5/2012 |
| CN | 202379991 U | 8/2012 |
| CN | 104919035 A | 9/2015 |
| CN | 105092543 A | 11/2015 |
| EP | 0471721 B1 | 4/1995 |
| EP | 0781291 B1 | 12/2004 |
| EP | 1704922 A2 | 9/2006 |
| EP | 2174715 A1 | 4/2010 |
| EP | 2695629 A2 | 2/2014 |
| EP | 3063524 | 1/2020 |
| EP | 3685918 A1 | 7/2020 |
| GB | 2344526 A | 6/2000 |
| JP | 2013525763 A | 6/2013 |
| JP | 2016527510 A | 9/2016 |
| TW | 207958 B | 6/1993 |
| TW | 201144037 A | 12/2011 |
| WO | WO-2004045772 A2 | 6/2004 |
| WO | WO-2009036956 A1 | 3/2009 |
| WO | WO-2009047804 A2 | 4/2009 |
| WO | WO-2010104292 A2 | 9/2010 |
| WO | WO-2011106315 A1 | 9/2011 |
| WO | WO-2011106384 A1 | 9/2011 |
| WO | WO-2011130629 A1 | 10/2011 |
| WO | WO-2012138177 A2 | 10/2012 |
| WO | WO-2013010178 A1 | 1/2013 |
| WO | WO-2013052318 A1 | 4/2013 |
| WO | WO-2014100725 A1 | 6/2014 |
| WO | WO-2014113785 A1 | 7/2014 |
| WO | WO-2015015175 A1 | 2/2015 |
| WO | WO-2015054245 A1 | 4/2015 |
| WO | WO-2015066540 A1 | 5/2015 |
| WO | WO-2016124907 A1 | 8/2016 |
| WO | WO-2017112911 A1 | 6/2017 |
| WO | WO-2017139447 A1 | 8/2017 |
| WO | WO-2019055875 | 3/2019 |
| WO | WO-2019055875 A2 | 3/2019 |
| WO | WO-2019118343 A2 | 6/2019 |
| WO | WO-2019143812 A1 | 7/2019 |
| WO | WO-2020191193 A1 | 9/2020 |
| WO | WO-2020257297 A1 | 12/2020 |
| WO | WO-2022061105 A1 | 3/2022 |

OTHER PUBLICATIONS

International preliminary report on patentability and search report dated Dec. 3, 2015 for PCT Application No. PCT/US14/63552.
International Search Report and Written Opinion dated Apr. 2, 2019 for PCT/US1851228.
ISR/WO dated Apr. 19, 2019 for PCT/US18/064736.
ISR/WO dated May 23, 2019 for PCT/US19/14005.
Notice of allowance dated Jan. 2, 2018 for U.S. Appl. No. 14/530,449.
Notice of Allowance dated Mar. 18, 2020 for U.S. Appl. No. 15/682,675.

(56) References Cited

OTHER PUBLICATIONS

Office action dated Mar. 25, 2016 for U.S. Appl. No. 14/530,449.
Office action dated Jun. 20, 2017 for U.S. Appl. No. 14/530,449.
Office action dated Aug. 10, 2016 for U.S. Appl. No. 14/530,449.
U.S. Appl. No. 14/530,449 Notice of Allowance dated Jan. 30, 2018.
Nov. 9, 2022 Notice of Allowance U.S. Appl. No. 17/479,391.
Mar. 29, 2022 Final Office Action U.S. Appl. No. 16/571,535.
Jun. 15, 2022 Non-Final Office Action U.S. Appl. No. 16/899,810.
Jun. 29, 2022 Non-Final Office Action U.S. Appl. No. 17/479,391.
Aug. 23, 2021 Non-Final Office Action U.S. Appl. No. 16/898,865.
Sep. 15, 2021 Non-Final Office Action U.S. Appl. No. 16/571,535.
Sep. 30, 2022 Final Office Action U.S. Appl. No. 16/571,535.
Corrected Notice of Allowability dated Jun. 30, 2020 for U.S. Appl. No. 15/682,675.
European Examination Report dated Aug. 4, 2021, for EP Application No. 18888874.7.
European Examination Report dated Oct. 8, 2018, for EP Appl. 14740636.7.
European search report with written opinion dated Aug. 22, 2016 for EP14740636.
Extended European Search Report dated Oct. 14, 2022 for EP20774341.0.
Extended European Search Report dated Apr. 28, 2020 for EP Application No. EP19216171.9.
Extended European Search Report dated Apr. 9, 2021 for EP Application No. EP18857231.
Extended European Search Report dated Jun. 7, 2022 for EP Application No. EP21210493.9.
International Preliminary Report on Patentability dated Mar. 26, 2020 for PCT Application No. PCT/US2018/051228.
International Preliminary Report on Patentability dated Jul. 21, 2015 for International Application No. PCT/US2014/012308.
International Preliminary Report on Patentability dated Jul. 21, 2020 for International Application No. PCT/US2019/014005.
International Preliminary Report on Patentability dated Jun. 16, 2020 for International Application No. PCT/US2018/064736.
International Preliminary Report on Patentability for corresponding PCT Application No. PCT/US2020/023630 dated Sep. 30, 2021.
International Preliminary Report on Patentability for PCT/US2020/038159 dated Dec. 30, 2021.
International Search Report and Written Opinion dated May 23, 2019 for International Application No. PCT/US2019/014005.
International Search Report and Written Opinion for corresponding PCT Application No. PCT/US2020/023630 dated Jun. 16, 2020.
International Search Report and Written Opinion for PCT/US2020/038159 dated Oct. 14, 2020.
International Search Report and Written Opinion for PCT/US2021/050862 dated Dec. 30, 2021.
International Search Report dated Jan. 21, 2015 for PCT Application No. PCT/US14/63552.
International search report with written opinion dated May 23, 2014 for PCT/US2014/012308.
Non-Final Office Action dated Sep. 4, 2019 for U.S. Appl. No. 15/682,675.
Notice of allowance dated Jan. 17, 2017 for U.S. Appl. No. 14/159,844.
Notice of allowance dated Oct. 12, 2016 for U.S. Appl. No. 14/159,844.
Notice of allowance dated Dec. 8, 2021 for U.S. Appl. No. 16/898,865.
Notice of allowance dated Sep. 11, 2019 for U.S. Appl. No. 15/436,080.
Notice of allowance dated Sep. 27, 2019 for U.S. Appl. No. 15/436,080.
Office action dated May 5, 2017 for U.S. Appl. No. 14/159,844.
Office action dated Nov. 5, 2015 for U.S. Appl. No. 14/159,844.
Office Action dated Jul. 27, 2016 issued in the corresponding Chinese Patent Application No. 201480010760.9.

* cited by examiner

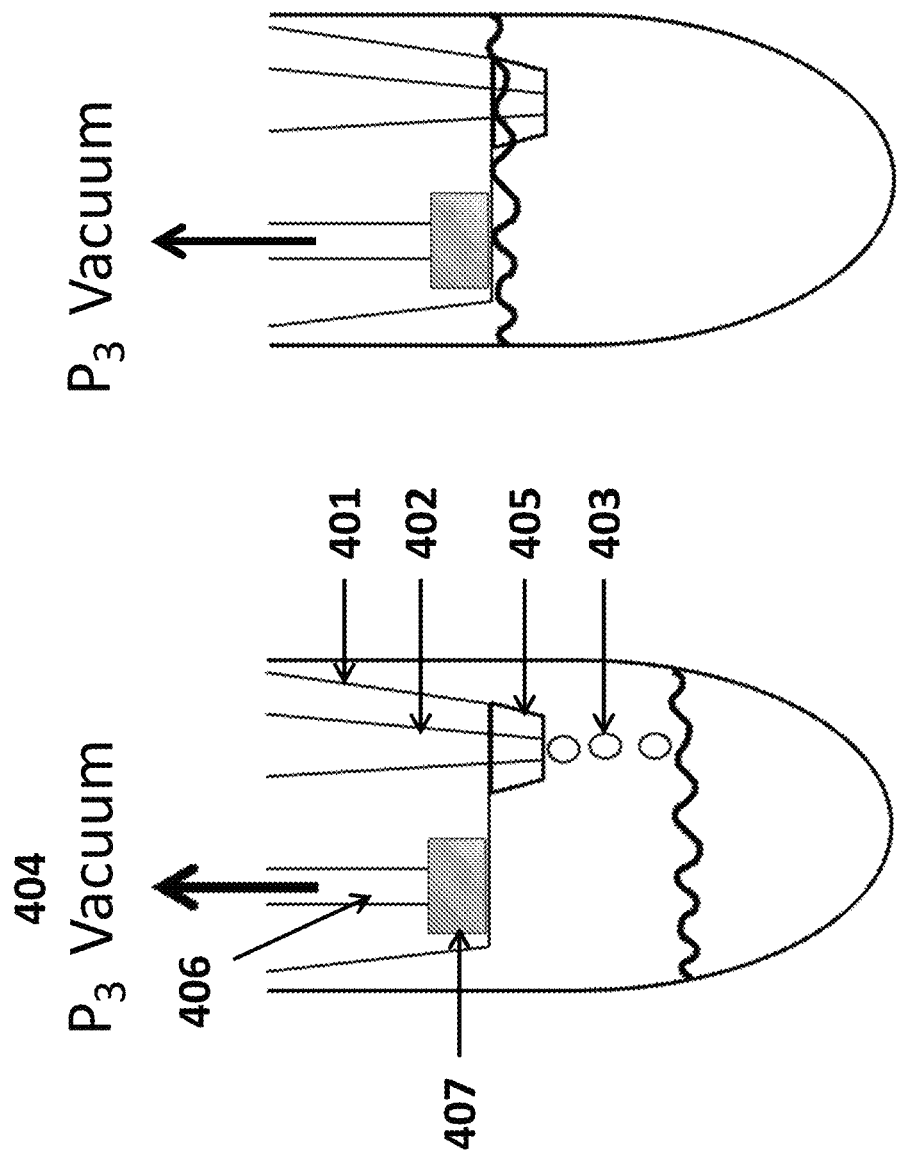

METHODS AND SYSTEMS FOR AUTOMATED SAMPLE PROCESSING

CROSS-REFERENCE

This application is a continuation application of PCT/US2018/051228 filed Sep. 14, 2018 which claims priority to U.S. Provisional Patent Application No. 62/559,173, filed Sep. 15, 2017, and U.S. Provisional Patent Application No. 62/688,861, filed Jun. 22, 2018, each of which is entirely incorporated herein by reference.

BACKGROUND

Laboratory testing has changed and improved remarkably, however, some assays may require manual labor for sample preparation. Sample preparation can include removal of the caps of containers containing samples or reagents, determining a type or measuring an amount of reagent necessary to process a sample, and pipetting one or more reagents together.

For example, a biological sample (e.g., saliva or blood) may be obtained from a subject and processed prior to conducting an assay on the biological sample to identify one or more targets in the biological sample. Such assay may include conducting polymerase chain reaction (PCR) on nucleic acid molecules from the biological sample. PCR may be conducted with using a primer set that is directed to particular targets.

The results of such assay may be directed to a user, such as the subject. The user may then use the results of the assay for various purposes, including identifying a disease (e.g., infectious disease or cancer).

SUMMARY

Recognized herein are various limitations associated with some methods for sample preparation. Sample preparation may be labor intensive, requiring multiple steps and operator involvement. Some labor-intensive steps can vary from one assay to another, leading to operator error and possible contamination of the sample by the operator. Manual processing of a sample may carry the risk of exposure of the operator to potentially dangerous biological chemicals.

In view of certain limitations of current methods for sample preparation, recognized herein is a need for a system that can automate the sample handling and sample preparation process for analytical procedures.

In some aspects, the present disclosure provides a system for sample processing. In some embodiments, the system can comprise a sample chamber. In some embodiments, the sample chamber can comprise a filter. In some embodiments, the filter can be configured to capture one or more nucleic acid molecules from a sample in the sample chamber. In some embodiments, the system can comprise a well fluidly coupled to the sample chamber by a first conduit. In some embodiments, the well can be configured to contain a reagent. In some embodiments, a fluid flow unit in fluid communication with the first conduit. In some embodiments, the fluid flow unit is configured to subject the reagent to flow from the well to the sample chamber. In some embodiments, the system can comprise one or more assay tubes. In some embodiments, a given assay tube of the one or more assay tubes can be fluidly coupled to the sample chamber via a second conduit. In some embodiments, the system can comprise a controller coupled to the fluid flow unit. In some embodiments, the controller can be configured to receive instructions from a mobile electronic device for processing of the sample. In some embodiments, in accordance with the instructions, the controller can be configured to direct the fluid flow unit to subject the reagent to flow from the well along the first conduit to the sample chamber. In some embodiments, in accordance with the instructions, the controller can be configured to provide a solution comprising the reagent and the one or more nucleic acid molecules in the sample chamber. In some embodiments, in accordance with the instructions, the controller can be configured to direct the fluid flow unit to subject the solution to flow from the sample chamber along the second conduit to the one or more assay tubes, such that the given assay tube receives at least a portion of the solution. In some embodiments, the system can further comprise a second fluid flow unit fluidly coupled to and disposed downstream of the one or more assay tubes. In some embodiments, the second fluid flow unit is fluidly connected to the one or more assay tubes by a third conduit. In some embodiments, the second fluid flow unit is configured to provide negative pressure to draw fluid from the sample chamber to at least one of the one or more assay tubes. In some embodiments, the second fluid flow unit is configured to provide positive pressure (e.g., pressure that is greater than a reference pressure, such as ambient pressure) to the sample chamber to generate bubbles in the sample, thereby subjecting the sample to mixing. In some embodiments, the second fluid flow unit is fluidly coupled to the atmosphere. In some embodiments, the system further comprises a waste chamber fluidly coupled to the sample chamber by a fourth conduit. In some embodiments, the system further comprises a third fluid flow unit disposed along the fourth conduit between the waste chamber and the sample chamber. In some embodiments, the third fluid flow unit is configured to draw the sample from the sample chamber to the waste chamber. In some embodiments, the sample is drawn from the sample chamber to the waste chamber through the filter, thereby capturing the one or more nucleic acids from the sample in the filter. In some embodiments, the system further comprises a valve disposed along the first conduit between the well and the sample chamber. In some embodiments, the valve is disposed upstream of the fluid flow unit along the first conduit. In some embodiments, the system further comprises a plurality of wells, including the well. In some embodiments, the system further comprises a plurality of valves, wherein a given valve of the plurality of valves is disposed along the first conduit between the plurality of wells and the sample chamber. In some embodiments, the reagent is a buffer that is selected from the group consisting of lysis buffer, wash buffer, a drying agent, and an elution buffer. In some embodiments, the lysis buffer contains salts, detergents, surfactants, or any combination thereof. In some embodiments, the lysis buffer contains salts, detergents, and surfactants. In some embodiments, the lysis buffer does not contain ethanol. In some embodiments, the lysis buffer contains ethanol. In some embodiments, the lysis buffer comprises two separate parts having a first part and a second part, wherein the first part contains slats, detergents, and surfactants, and the second part contains ethanol. In some embodiments, at least one of the sample chamber, the well, and the waste chamber comprises a seal. In some embodiments, the seal comprises at least one layer. In some embodiments, the at least one layer comprises polypropylene, adhesive, or aluminum. In some embodiments, the given assay tube comprises a cap, and at least a portion of the second conduit between the sample chamber and the given assay tube is disposed in the cap. In some embodiments, an end of the second conduit along an inner surface of the cap comprises a tip. In some embodiments, at least a portion of the second conduit is disposed in the tip. In some embodiments, a cross-sectional area of the second conduit decreases along an axial length of the tip. In some embodiments, the one or more assay tubes comprise a plurality of assay tubes, and wherein a cross-sectional area of a portion of the second conduit in the tip is different in at least two of the plurality of assay tubes. In some embodiments, the given assay tube comprises a cap, and wherein the third conduit between the given assay tube and the second fluid flow unit is disposed in the cap. In some embodiments, an end of the third conduit along an inner surface of the cap comprises a molecular sieve. In some embodiments, the molecular sieve is porous. In some embodiments, the molecular sieve is permeable to a gas. In some embodiments, the molecular sieve is hydrophobic. In some embodiments, the cap extends into the given assay tube. In some embodiments, the cap extends into the given assay tube to a depth that determines a maximum working volume of the assay tube. In some embodiments, the depth of the cap is different than another depth of another cap extending into another assay tube of the one or more assay tubes. In some embodiments, the cap is removably coupled to the given assay tube. In some embodiments, the given assay tube comprises one or more pairs of primers for performing an assay to detect a target nucleic acid molecule. In some embodiments, the assay is polymerase chain reaction. In some embodiments, the system further comprises a heater in thermal communication with the sample chamber, wherein the heater is configured to subject a sample in the given assay tube to heating. In some embodiments, the heater further comprises a spring-loaded plate. In some embodiments, the spring-loaded plate provides improved thermal contact with the sample chamber compared with a heater without such spring-loaded plate. In some embodiments, the heater is configured to subject the sample to heating as part of one or more heating and cooling cycles. In some embodiments, the fluid flow unit is a pump or a compressor. In some embodiments, the fluid flow unit comprises one or more pumps. In some embodiments, the one or more pumps include a first pump and a second pump, wherein the first pump is configured to subject the reagent to flow from the well to the sample chamber, and wherein the second pump is configured to subject the solution to flow from the sample chamber to the one or more assay tubes. In some embodiments, the fluid flow unit comprises one or more compressors. In some embodiments, the system further comprises a sample processing unit comprising a dock, wherein the sample processing unit comprises the fluid flow unit, wherein the well and the sample chamber are included in a sample processing cartridge, and wherein the dock is configured to receive the cartridge to bring the well and the sample chamber in fluid communication with the fluid flow unit. In some embodiments, the controller is configured to come in wireless communication with the mobile electronic device. In some embodiments, the fluid flow unit (e.g., pump) includes or is coupled to a pressure sensor.

In some aspects, the present disclosure provides a method for sample processing, comprising activating a system. In some embodiments, the system can comprise a sample chamber comprising a filter configured to capture one or more nucleic acid molecules from a sample in the sample chamber. In some embodiments, the system can comprise a well fluidly coupled to the sample chamber by a first conduit, wherein the well is configured to contain a reagent. In some embodiments, the system can comprise a fluid flow unit in fluid communication with the first conduit, wherein the fluid flow unit is configured to subject the reagent to flow from the well to the sample chamber. In some embodiments, the system can comprise one or more assay tubes, wherein a given assay tube of the one or more assay tube is fluidly coupled to the sample chamber via a second conduit. In some embodiments, the system can comprise a controller coupled to the fluid flow unit, wherein the controller is configured to receive instructions from the mobile electronic device for processing of the sample. In some embodiments, the method comprises using the controller to receive the instructions from the mobile electronic device. In some embodiments, the method can comprise, in accordance with the instructions, using the controller to (i) direct the fluid flow unit to subject the reagent to flow from the well along the first conduit to the sample chamber, to provide a solution comprising the reagent and the one or more nucleic acid molecules in the sample chamber, and (ii) direct the fluid flow unit to subject the solution to flow from the sample chamber along the second conduit to the one or more assay tubes, such that the given assay tube receives at least a portion of the solution. In some embodiments, the system further comprises at least one heating unit, wherein the at least one heating unit is in thermal communication with the one or more assay tubes including the given assay tube, and wherein in accordance with the instructions, the controller directs the at least one heating unit to subject the solution to heating. In some embodiments, the controller directs the at least one heating unit to subject the solution to one or more heating and cooling cycles. In some embodiments, the system comprises a sample processing unit comprising a dock, wherein the sample processing unit comprises the fluid flow unit, wherein the well and the sample chamber are included in a sample processing cartridge, and wherein (a) comprises the dock receiving the cartridge to bring the well and the sample chamber in fluid communication with the fluid flow unit. In some embodiments, the controller is configured to come in wireless communication with the mobile electronic device.

In some aspects, the present disclosure provides a sample processing cartridge comprising a sample chamber. In some embodiments, the sample chamber can comprise a filter configured to capture one or more nucleic acid molecules from a sample in the sample chamber. In some embodiments, the cartridge can comprise a well fluidly coupled to the sample chamber by a first conduit, the well configured to contain a reagent. In some embodiments, the cartridge can comprise one or more assay tubes, wherein a given assay tube of the one or more assay tube is fluidly coupled to the sample chamber via a second conduit. In some embodiments, the cartridge can comprise a first opening fluidly connected with the first conduit, the first opening configured to fluidly connect a fluid flow unit to the first conduit, wherein the fluid flow unit is coupled to a controller, wherein the controller is configured to receive instructions from a mobile electronic device for processing of the sample, and in accordance with the instructions, (i) direct the fluid flow unit to subject the reagent to flow from the well along the first conduit to the sample chamber, to provide a solution comprising the reagent and the one or more nucleic acid molecules in the sample chamber, and (ii) direct the fluid flow unit to subject the solution to flow from the sample chamber along the second conduit to the one or more assay tubes, such that the given assay tube receives at least a portion of the solution. In some embodiments, the sample processing cartridge further comprises a second fluid flow unit fluidly coupled to and disposed downstream of the one or more assay tubes. In some embodiments, the second fluid flow unit is fluidly connected to the one or more assay tubes by a third conduit. In some embodiments, the sample processing cartridge further comprises a waste chamber fluidly coupled to the sample chamber by a fourth conduit. In some embodiments, the sample processing cartridge further comprises a snorkel connected to the sample chamber. In some embodiments, the waste chamber is further connect to a third fluid flow unit. In some embodiments, the third fluid flow unit is disposed along the fourth conduit between the waste chamber and the sample chamber. In some embodiments, the third fluid flow unit is disposed downstream from the waste chamber. In some embodiments, the sample processing cartridge further comprises a shroud. In some embodiments, the fluid flow unit is a pump. In some embodiments, the pump is a multi-directional pump. In some embodiments, the fluid flow unit is coupled to a pressure sensor.

In some aspects, the present disclosure provides a sample processing system. In some embodiments, the sample processing system comprises a first fluid flow path. In some embodiments, the sample processing system comprises a first pump and a second pump in fluid communication with the first fluid flow path. In some embodiments, the first pump and the second pump are multi-directional pumps. In some embodiments, the first pump and the second pump are configured to subject fluid in the first fluid flow path to flow along a first direction and a second direction, which second direction is different than the first direction. In some embodiments, the sample processing system further comprises a dock configured reversibly engage with a cartridge comprising a second fluid flow path in fluid communication with one or more reagents. In some embodiments, the dock is configured to bring the first fluid path in fluid communication with the second fluid flow path subsequent to engagement with the cartridge. In some embodiments, the first fluid flow path does not include any valves. In some embodiments, the sample processing system further comprises a controller operatively coupled to the at least two multi-directional pumps. In some embodiments, the controller is configured to direct each of the at least two multi-directional pumps to subject the fluid in the first fluid flow path to flow along the first direction and the second direction. In some embodiments, the sample processing system further comprises a lid comprising a body configured to come in contact with the cartridge when the dock has reversibly engaged with the cartridge. In some embodiments, the lid is coupled to a housing comprising the first fluid flow path and the at least two multi-directional pumps. In some embodiments, the lid is configured to move towards the housing from (i) a first position in which the body contacts the cartridge, to (ii) a second position in which the first fluid path is brought in fluid communication with the second fluid flow path. In some embodiments, the lid is configured to rotate relative to the housing. In some embodiments, each of the at least two multi-directional pumps is configured to supply positive pressure and negative pressure (e.g., vacuum) in the first fluid flow path. In some embodiments, each of the at least two multi-directional pumps is configured to subject the fluid in the first fluid flow path to flow along a first direction and a second direction. In some embodiments, the sample processing system further comprises a third pump configured to come in fluid communication with the second fluid flow path when the dock has reversibly engaged with the cartridge.

In some aspects, the present disclosure provides a method for processing a sample. In some embodiments, the method comprises: activating a system comprising a first fluid flow path. In some embodiments, the system comprises a first pump and a second pump in fluid communication with the first fluid flow path. In some embodiments, the first pump and the second pump are multi-directional pumps. In some embodiments, the first pump and the second pump are configured to subject fluid in the first fluid flow path to flow along a first direction and a second direction, which second direction is different than the first direction. In some embodiments, the system further comprises a dock. In some embodiments, the method further comprising engaging the dock with a cartridge comprising a second fluid flow path in fluid communication with one or more reagents. In some embodiments, subsequent to engagement of the dock with the cartridge, the first fluid path is in fluid communication with the second fluid flow path. In some embodiments, the method further comprises using the system and the one or more reagents to process the sample. In some embodiments, the method further comprises removing the cartridge from the docket subsequent to processing the sample. In some embodiments, the sample is a biological sample.

In some aspects, the present disclosure provides a system for processing a sample. In some embodiments, the system comprises at least two multi-directional pumps in fluid communication with a fluid flow path for processing the sample, which fluid flow path does not include any valves.

In some embodiments, a direction of fluid flow along the fluid flow path is controlled upon regulation of pressure in the fluid flow path by the at least two multi-directional pumps. In some embodiments, the at least two multi-directional pumps comprise three multi-directional pumps.

In some embodiments, the present disclosure provides a method for processing a sample. In some embodiments, the method comprises activating a system comprising at least two multi-directional pumps in fluid communication with a fluid flow path for processing the sample, which fluid flow path does not include any valves. In some embodiments, the method further comprises subjecting fluid in the fluid flow path to flow along a first direction upon application of a first pressure drop by a first multi-directional pump of the at least two multi-directional pumps and a second pressure drop by a second multi-directional pump of the at least two multi-directional pumps. In some embodiments, the method further comprises subjecting fluid in the fluid flow path to flow along a second direction different than the first direction upon application of a third pressure drop by the first multi-directional pump and a fourth pressure drop by the second multi-directional pump. In some embodiments, the first pressure drop is different than the second pressure drop. In some embodiments, the third pressure drop is different than the fourth pressure drop. In some embodiments, the first pressure drop is different than the third pressure drop, or the second pressure drop is different than the fourth pressure drop. In some embodiments, the first pressure drop is different than the third pressure drop, and the second pressure drop is different than the fourth pressure drop.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4A shows a cross-sectional view of an assay tube being filled in a dropwise fashion with sample drawn from the sample chamber.

FIG. 4B shows a cross-sectional view of an assay tube filled with sample drawn from the sample chamber.

DETAILED DESCRIPTION

Figure 1A:
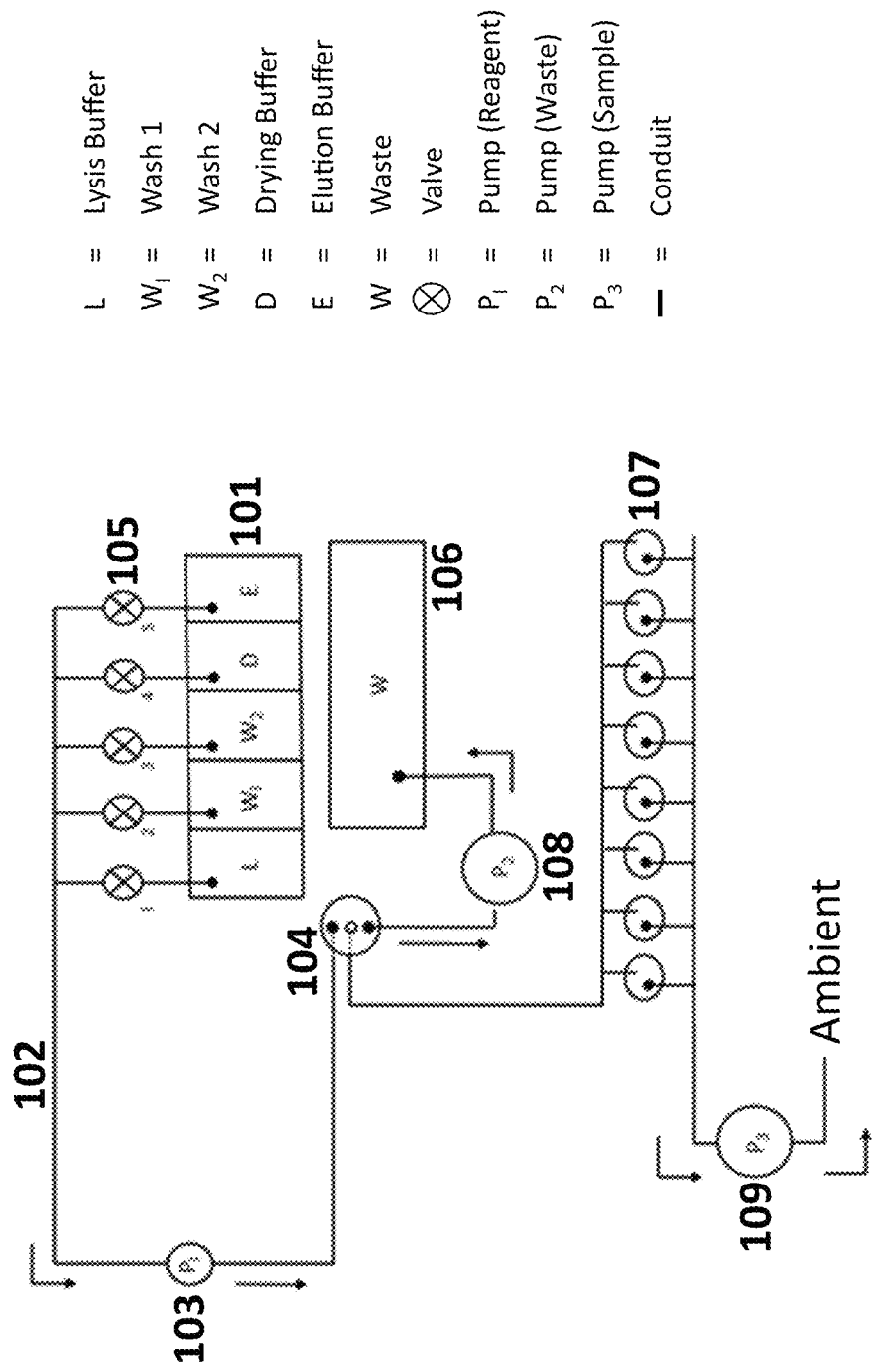
FIG. 1A shows a schematic of an example of an automated sample preparation system. As shown in this figure, L indicates lysis buffer; $W_1$ indicates wash 1; $W_2$ indicates wash 2; D indicates drying buffer; E indicates elution buffer; W indicates waste; a circle symbol with an X inside indicates valve; $P_1$ indicates pump (reagent); $P_2$ indicates pump (waste); $P_3$ indicates pump (sample); and the lines indicate conduits.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "fluid flow unit," as used herein, generally refers to one or more devices that are configured to subject a fluid to flow. A fluid flow unit may include a pump or a plurality of pumps. Alternative or in addition to, the fluid flow unit may include a compressor or a plurality of compressors. The fluid flow unit may include other elements that are configured to subject a fluid to flow, such as deformable membranes that are configured to subject a fluid to flow in a channel upon actuation.

The term "sample," as used herein, generally refers to a sample for processing. The sample may be a biological sample. The sample may include one or more nucleic acid molecules, such as deoxyribonucleic acid (DNA), ribonucleic acid (RNA), and/or protein. The RNA may be messenger RNA. The DNA may be genomic DNA. The DNA may be a fragment of a larger DNA sample.

The sample may be a soil sample. The sample may be a tissue or fluid sample from a subject, such as saliva, semen, blood (e.g., whole blood), serum, synovial fluid, tear, urine, or plasma. The sample may be a tissue sample, such as a skin sample or tumor sample. The sample may be obtained from a portion of an organ of a subject. The sample may be a cellular sample. The sample may be a cell-free sample.

The term "subject," as used herein, generally refers to an individual from whom a sample is obtained for processing. The subject may be a patient. The subject may not be a patient. The subject may be an individual in need of treatment. The subject may be an individual having or displaying a disease condition or suspected of having the disease condition. The subject may be an individual who does not have, is not displaying, or is not suspected of having a disease condition.

The term "conduit," as used herein, generally refers to a fluid flow path that is configured to direct a fluid from one point to another. A conduit may be a channel or a plurality of channels. The conduit may be a microfluidic channel or a plurality of microfluidic channels. A cross-sectional area of a conduit may be about 0.01 mm$^2$, about 0.05 mm$^2$, about 0.1 mm$^2$, about 0.2 mm$^2$, about 0.3 mm$^2$, about 0.4 mm$^2$, about 0.5 mm$^2$, about 0.6 mm$^2$, about 0.7 mm$^2$, about 0.8 mm$^2$, about 0.9 mm$^2$, about 1.0 mm$^2$, about 1.1 mm$^2$, about 1.2 mm$^2$, about 1.3 mm$^2$, about 1.4 mm$^2$, about 1.5 mm$^2$, about 1.6 mm$^2$, about 1.7 mm$^2$, about 1.8 mm$^2$, about 1.9 mm$^2$, about 2.0 mm$^2$, about 3.0 mm$^2$, about 4.0 mm$^2$, about 5.0 mm$^2$, about 10 mm$^2$, about 15 mm$^2$, about 20 mm$^2$, about 25 mm$^2$, or greater than about 25 mm$^2$. A shape of a cross section of a conduit may be a triangle (e.g., an equilateral triangle, an isosceles triangle, a scalene triangle, a right triangle, an acute triangle, or an obtuse triangle), a square, a rectangle, a diamond, a rhombus, a parallelogram, a kite, a trapezoid, a pentagon, a hexagon, a heptagon, an octagon, a nonagon, a decagon, a shape having greater than 10 sides, a circle, an oval, an egg shape, or a droplet shape.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Analysis of biological sample-derived materials may not occur until the sample is processed through numerous pre-analysis steps. Often, the preparation process is time consuming, laborious, and can be subject to human error. For example, immuno- and molecular-biological diagnostic assays on clinical samples, such as blood or tissue cells, may require separation of the molecules of interest from the crude sample by disrupting or lysing the cells to release such molecules including proteins and nucleic acids (i.e., DNA and RNA) of interest, followed by purification of such proteins and/or nucleic acids. Only after performing processing steps can analysis of the molecules of interest begin. Additionally, protocols used for the actual analysis of the samples require numerous more steps before useful data is obtained. The present disclosure provides devices, systems, methods and kits for the automated or substantially automated processing of biological samples.

The present disclosure also provides devices, systems, methods and kits for sample preparation and processing. Such devices, systems, methods and kits may permit the automated processing of biological samples in a lab-free environment. Devices and systems of the present disclosure may be portable, allowing users to employ such devices in remote locations, for example.

FIGS. 1A-1D schematically illustrate examples of systems for sample preparation and/or analysis.

FIG. 1A schematically illustrates a system for sample preparation. The system includes reagent chambers 101 that are fluidly connected by conduits 102 to a first pump 103 capable of applying a draw pressure (or pressure drop) to transfer fluid from the reagent chambers to a sample chamber 104. The draw pressure may be selectively applied to one or more chambers by opening valves 105 disposed along the conduit between the reagent chamber and the pump. Fluid from the sample chamber may be transferred to the waste chamber 106, or to one or more assay tubes 107 for further analysis, using a second pump 108 or third pump 109.

Figure 1B:
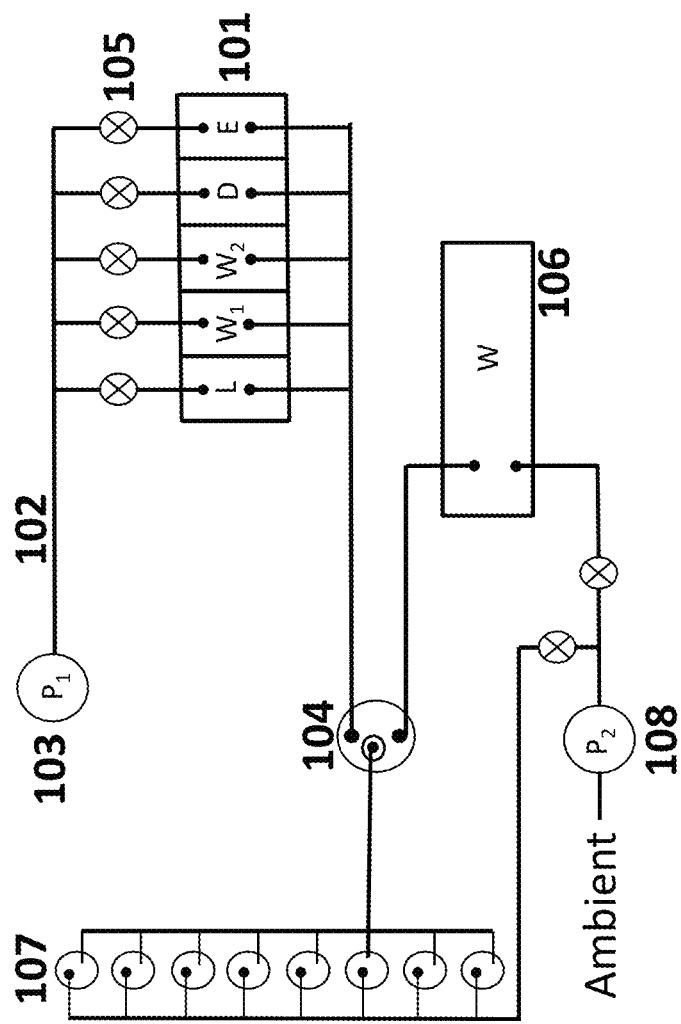
FIG. 1B shows a schematic of an example of an automated sample preparation system. As shown in this figure, L indicates lysis buffer; $W_1$ indicates wash 1; $W_2$ indicates wash 2; D indicates drying buffer; E indicates elution buffer; W indicates waste; a circle symbol with an X inside indicates valve; $P_1$ indicates pump (reagent); $P_2$ indicates pump (sample); and the lines indicate conduits.

FIG. 1B schematically illustrates another system for sample preparation. The system includes reagent chambers 101 that are fluidly connected by conduits 102 to a first pump 103 capable of applying a positive pressure (e.g., pressure that is greater than a reference pressure, such as ambient pressure) to push fluid from the reagent chambers to a sample chamber 104. In this arrangement, as compared the system of FIG. 1A, the first pump does not contact the fluid in the reagent chambers. The positive pressure may be selectively applied to one or more chambers by opening valves 105 disposed along the conduit between the reagent chamber and the pump. Fluid from the sample chamber may be transferred to the waste chamber 106, or to one or more assay tubes 107 for further analysis, using a second pump 108. Yet another system comprising a first pump as shown in FIG. 1A (e.g., configured to draw fluid from the reagent chambers) and a second pump as shown in FIG. 1B (e.g., configured to draw fluid from the sample chamber) is also contemplated.

Figure 1C:
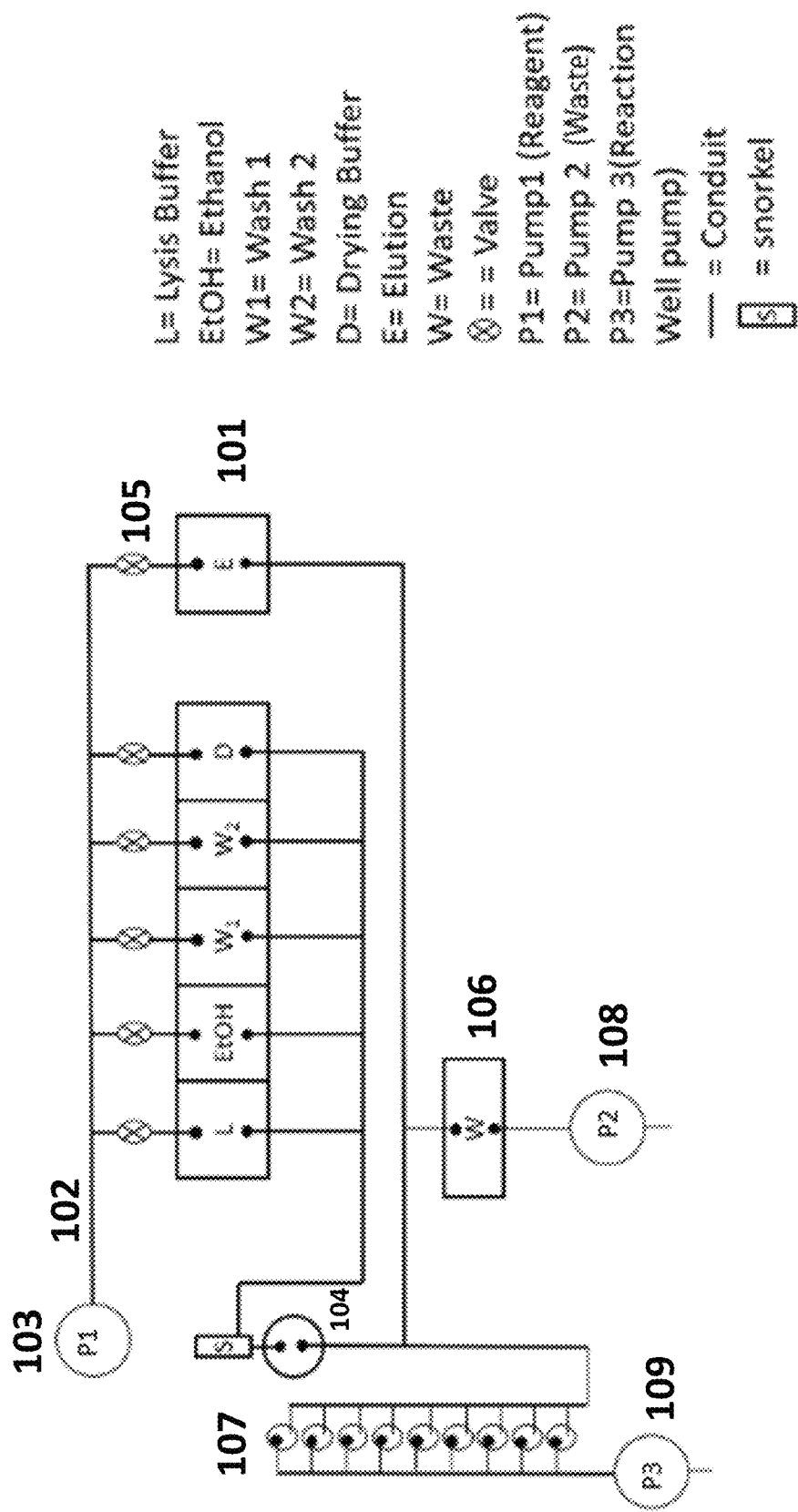
FIG. 1C shows a schematic of an example of an automated sample preparation system. As shown in this figure, L indicates lysis buffer; EtOH indicates Ethanol; $W_1$ indicates wash 1; $W_2$ indicates wash 2; D indicates drying buffer; E indicates elution buffer; W indicates waste; a circle symbol with an X inside indicates valve; $P_1$ indicates pump 1 (reagent); $P_2$ indicates pump 2 (waste); $P_3$ indicates pump 3 (reaction well pump); the lines indicate conduits; and a rectangle symbol with an S inside indicates snorkel.
Figure 14:
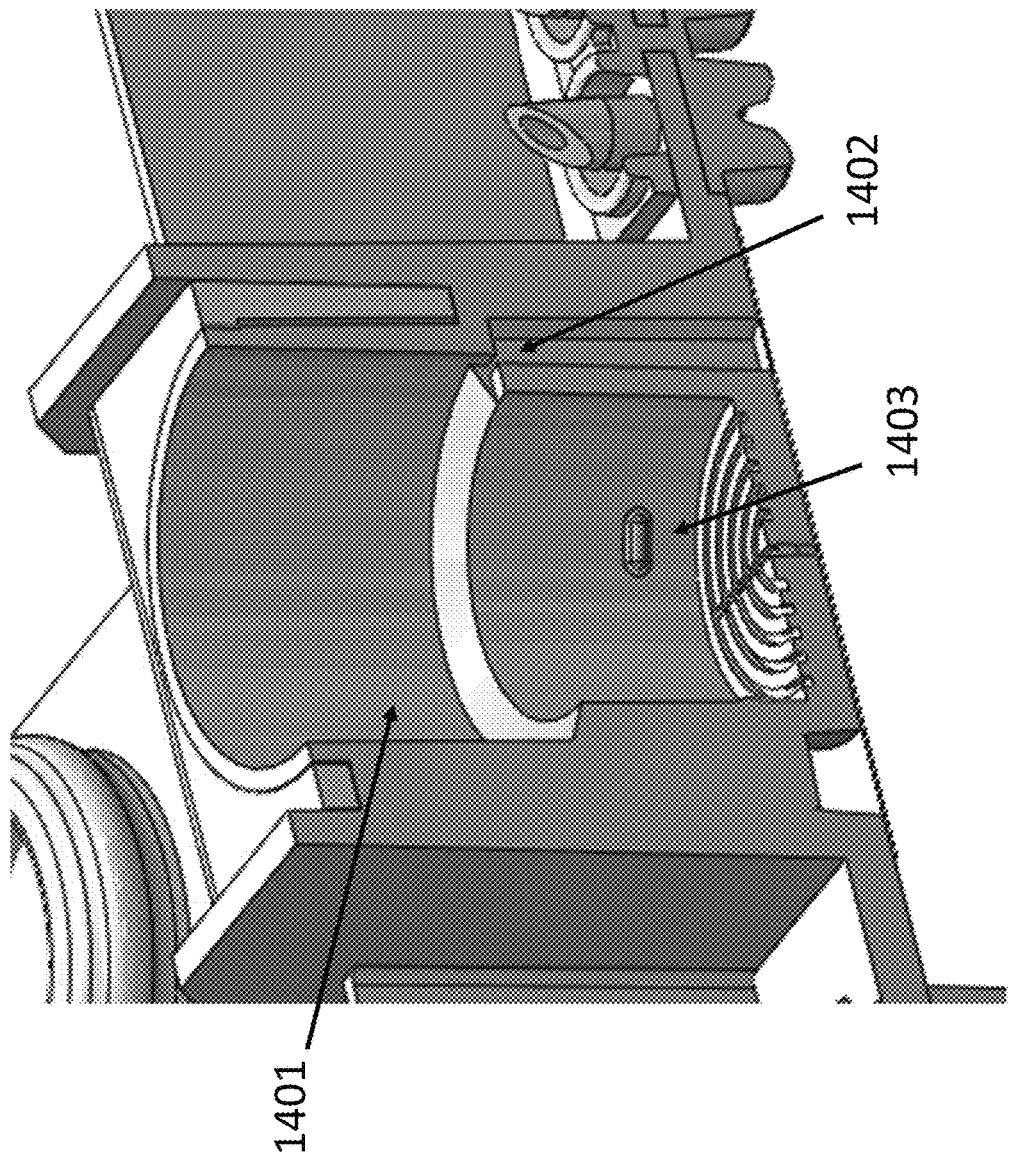
FIG. 14 shows an example cross-section view of the sample chamber connected to a snorkel.

FIG. 1C schematically illustrates another system for sample preparation. The system includes reagent chambers 101 that are fluidly connected by conduits 102 to a first pump 103 capable of applying a positive pressure to push fluid from the reagent chambers to a sample chamber 104. In this arrangement, the cartridge comprises six reagent chambers. Besides the five reagent chambers similar to the systems shown in FIGS. 1A and 1B, an additional reagent chamber is included for an additional reagent, for example, ethanol. This additional reagent chamber may include an elution buffer, for example. Also in this arrangement, the first pump 103 does not contact the fluid in the reagent chambers. The positive pressure may be selectively applied to one or more chambers by opening valves 105 disposed along the conduit between the reagent chamber and the pump. A sample chamber 104 can be connected to reagent chambers through one or more conduits. As shown here in FIG. 1C, a main conduit connecting the sample chamber and the reagent chambers can further comprise a snorkel. Fluid from the sample chamber 104 may be transferred to the waste chamber 106 using a second pump 108, or to one or more assay tubes 107 using a third pump 109 for analysis. As an alternative, a single pump and one or more valves may be used to draw fluid from the sample chamber 104 into the waste chamber 106 or the one or more assay tubes 107 (see, e.g., FIG. 1B). An example of a sample chamber 1401 connected to a snorkel 1402 is shown in FIG. 14. The snorkel 1402 can have a ventilating function and it can connect the sample chamber 1401 to the ambient air. The part 1403 shown in this figure is a pump to capture a filter stack. Examples of the filter stack include, but are not limited to, hydrophilic porous support, porous Glass filter, or hydrophobic porous support.

Figure 1D:
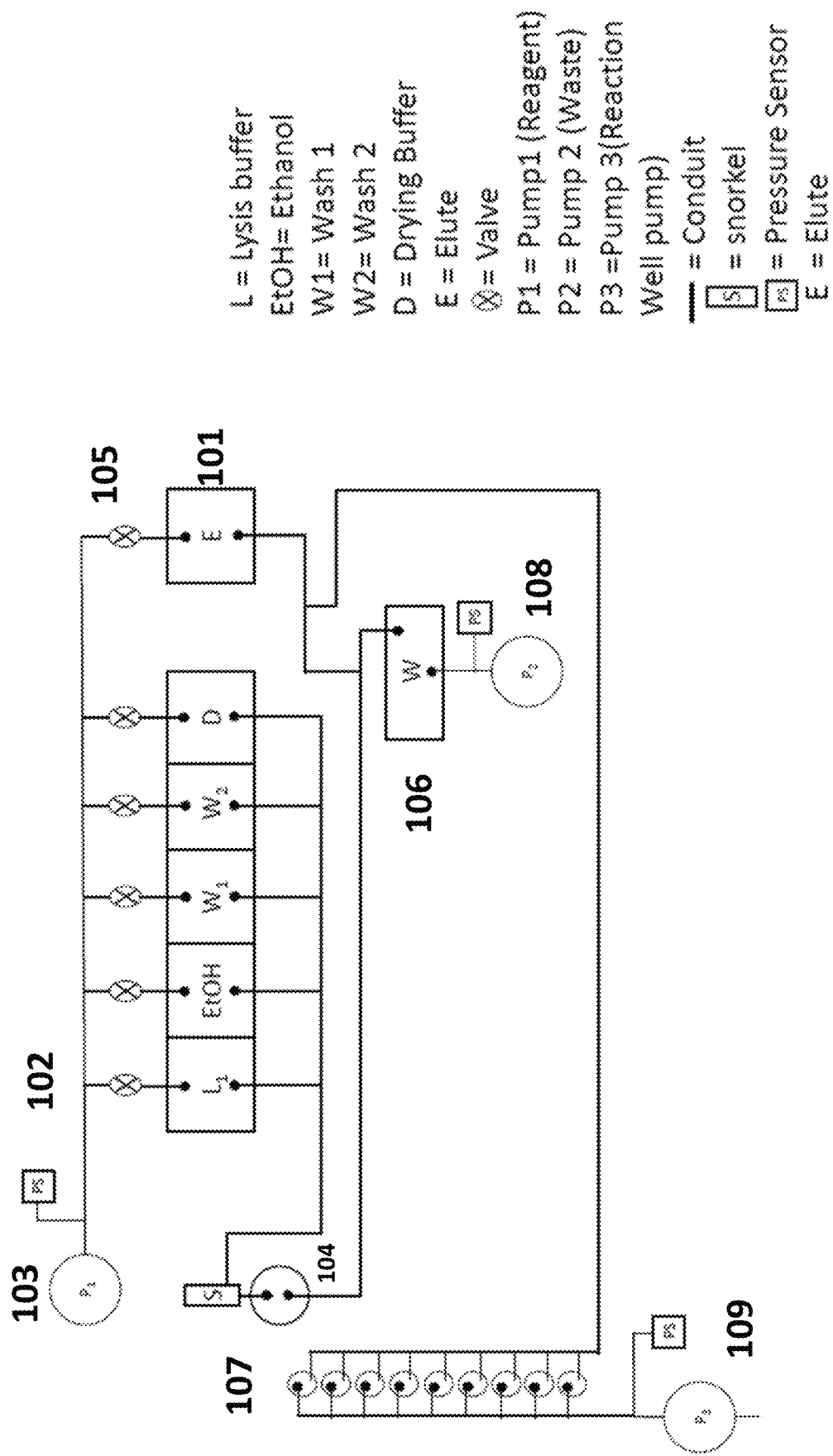
FIG. 1D shows a schematic of an example of an automated sample preparation system. As shown in this figure, $L_1$ indicates lysis buffer; EtOH indicates Ethanol; $W_1$ indicates wash 1; $W_2$ indicates wash 2; D indicates drying buffer; E indicates elution buffer; a circle symbol with an X inside indicates valve; $P_1$ indicates pump 1 (reagent); $P_2$ indicates pump 2 (waste); $P_3$ indicates pump 3 (reaction well pump); the lines indicate conduits; a rectangle symbol with an S inside indicates snorkel; and a square symbol with PS inside indicates pressure sensor.

FIG. 1D schematically illustrates another system for sample preparation. The system includes reagent chambers 101 that are fluidly connected by conduits 102 to a first pump 103 capable of applying a positive pressure to push fluid from the reagent chambers to a sample chamber 104. Similar to the system shown in FIG. 1C, in this arrangement, the cartridge comprises six reagent chambers containing five reagent chambers similar to the systems shown in FIGS. 1A and 1B and an additional reagent chamber. In this arrangement, the first pump 103 does not contact the fluid in the reagent chambers. The positive pressure may be selectively applied to one or more chambers by opening valves 105 disposed along the conduit between the reagent chamber and the pump. A sample chamber 104 can be connected to reagent chambers through one or more conduits. A main conduit connecting the sample chamber and the reagent chambers can further comprise a snorkel. Fluid from the sample chamber 104 may be transferred to the waste chamber 106 using a second pump 108, or to one or more assay tubes 107 using a third pump 109 for analysis. As an alternative, a single pump and one or more valves may be used to draw fluid from the sample chamber 104 into the waste chamber 106 or the one or more assay tubes 107.

Although FIGS. 1A-1D illustrate examples of pump and valve configurations, Various pump and/or valve configurations may be used, such as, for example, "wet pumps" (e.g., pumps configured to contact a fluid) and/or "dry pumps" (e.g., pumps configured to not contact a fluid) may be used in systems of the present disclosure. In addition, other units for effecting fluid flow may be used, such as one or more compressors and/or one or more compressors together with one or more pumps.

The pumps 103, 108 and 109 may be configured to supply a negative pressure (e.g., vacuum). As an alternative, the pumps 103, 108 and 109 may be configured to supply positive pressure. As another alternative, the pumps 103, 108 and 109 may be configured to supply both negative pressure and positive pressure in alternative modes of operations, which may be used to subject a fluid along a first direction and subsequently along a second direction different from (e.g., opposite of) the first direction. The pumps 103, 108 and 109 may be multi-directional (e.g., bi-directional) pumps, each configured to operate in a first mode in which negative pressure is applied to a fluid flow path and a second mode in which positive pressure is applied to the fluid flow path. Such pumps may have other modes in which a range of pressures (or pressure drops) are applied.

The systems described herein may comprise various numbers of pumps. In some cases, the systems comprise 2 or 3 pumps as illustrated in FIGS. 1A-1D. In some other cases, the systems comprise one pump. In some other cases, the systems comprise 4, 5, 6, 7, 8, 9, 10, or more pumps. In some cases, the systems comprise at least 1, at least 2, at least 3, at least 4, at least 5, at least 6, at least 7, at least 8, at least 9, at least 10, at least 20, at least 30, at least 40, or more pumps.

The valves 105 may be actuated by various approaches. Such approaches include pneumatic actuation, such as with the aid of positive pressure or negative pressure from a source of positive pressure or negative pressure, respectively. Positive pressure may be provided using one or more compressors. Negative pressure may be provided using one or more pumps. In another approach, valves may be actuated using electrothermal heating. For example, a valve can be a shape memory valve. A shape memory valve may refer to any type of valve that comprises a material that "remembers" its original shape and is capable of returning to its pre-deformed shape when heated. In some cases, the shape memory valve can comprise a nitinol or Nickel Titanium wire that actuates a seal during contraction upon electrothermal heating. In some cases, the shape memory valve can comprise a copper-aluminum-nickel wire that actuates a seal during contraction upon electrothermal heating. In yet another approach, valves may be actuated using electromechanical units. For example, the valve can be a solenoid valve. An electromechanical valve can refer to any type of valve that is controlled by an electric current (e.g., through a solenoid). In some cases, the solenoid valve may be a latching solenoid valve. In the case of a two-port valve, flow may be switched on or off. In the case of a three-port valve, outflow may be switched between any or both of the one or more outlet ports. The numbers of valves shown in FIGS. 1A-1D are non-limiting examples. The systems may comprise various numbers of valves. In some cases, the systems do not comprise any valve. In some cases, the systems comprise more valves than the systems shown in FIGS. 1A-1D. For example, the systems may comprise at least 1, at least 2, at least 3, at least 4, at least 5, at least 6, at least 7, at least 8, at least 9, at least 10, at least 20, at least 30, at least 40, or more valves.

The conduits may have various dimensions. In some examples, the conduits 102 have dimensions on the order of micrometers. In such cases, the conduits 102 may be part of a microfluidic device.

Although the systems of FIGS. 1A-1D include a certain number of reagent chambers, systems of the present disclosure may include at least 1, 2, 3, 4, 5, 6, 7, 8, 9, 10, 15, 20, or more chambers, which may be reagents chambers. A given chamber may house or contain a reagent. As an alternative or in addition to, a given chamber may be used for conducting a reaction or mixing.

Figure 6:
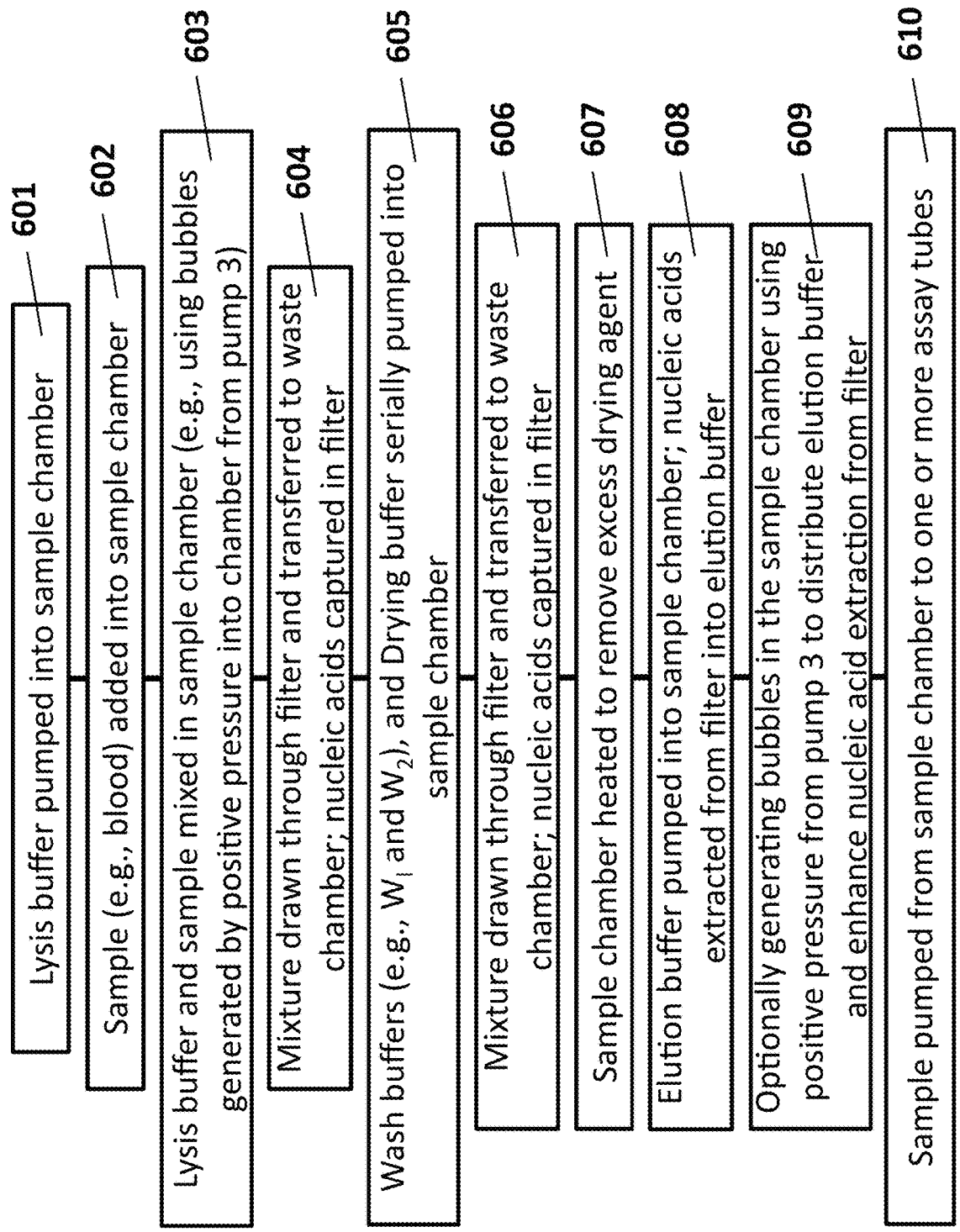
FIG. 6 shows a flow chart of an example method of preparing a sample using a sample preparation device or system of the present disclosure, such as the system of FIGS. 1A-B.

FIG. 6 shows an example process flow for using the system of FIGS. 1A-D. In a first operation 601, a valve 105 is opened and lysis buffer is pumped from a reagent chamber 101 into the sample chamber 104. In a second operation 602, a sample to be analyzed is added into the sample chamber 104 now containing the lysis buffer. Filling the sample chamber 104 with a buffer (e.g., a lysis buffer) prior to adding the sample may prevent loss of target nucleic acids within the sample (e.g., due to adhesion along the wall of the sample chamber). In a third operation 603, the lysis buffer and the sample are mixed in sample chamber 104. The mixing can be performed in a variety of ways. In an example, bubbles can be generated by positive pressure into the sample chamber from a pump (e.g., first pump 103, second pump 108, or third pump 109). Although any pump of the device may be used to generate bubbles within the sample chamber 104, the pump 109 may be used to avoid situations in which reversing the flow of the second pump 108 (e.g., the waste pump), for example, may increase the risk of contamination of the sample in the sample chamber 104 with waste from the waste chamber 106. Other techniques may also be used to mix lysis buffer and sample in the sample chamber 104, such as agitating the chamber 101 or the entire device.

In a subsequent operation 604 the mixture of sample and lysis buffer is drawn through a filter 302 by the second pump 108, thereby capturing targets (e.g., nucleic acids) in the filter 302 and transferring waste to a waste chamber 106. In a subsequent operation 605, one or more wash buffers (e.g., FIGS. 1A-D, labels $W_1$ and $W_2$), and/or drying buffers (e.g., FIGS. 1A-D, label D), are serially pumped into sample chamber 104, and mixed with the targets captured in the filter 302. Subsequently, in operation 606, the mixture of buffer and target is drawn through the filter 302 by pump 108, thereby capturing targets (e.g., nucleic acids) in the filter 302 and transferring waste to a waste chamber 106. In some cases, in operation 607, following washing of the targets captured in the filter 302 with a drying buffer (e.g., a volatile chemical such as acetone), the sample chamber may be heated (e.g., using a heating pad disposed along an outer surface of the sample chamber) to remove residual drying buffer (e.g., through vaporization). This may reduce contamination of the target by the drying agent. In a subsequent operation 608, elution buffer is pumped into sample chamber, thereby extracting a target (e.g., nucleic acids) from the filter into the elution buffer. In another operation 609, bubbles can be generated by positive pressure into the sample chamber from a pump to distribute the elution buffer throughout the sample chamber, and enhance extraction of the target from the filter. In yet another operation 610, the mixture of elution buffer (e.g., FIGS. 1A-C, label E) and target is pumped by the third pump 109 from the sample chamber 104 to one or more assay tubes 107 for further processing and/or analysis.

Samples

A variety of samples (e.g., biological samples) may be processed. A sample can be obtained invasively (e.g., tissue biopsy) or non-invasively (e.g., venipuncture). In some embodiments, a sample may be obtained from the environment (e.g., a water sample from a river or stream, or a soil sample). In some embodiments, a sample can be a solid sample or a liquid sample. In some embodiments, a sample can be a biological sample or a non-biological sample. In some embodiments, a sample can comprise an in-vitro sample or an ex-vivo sample. Non-limiting examples of a sample include an amniotic fluid, bile, bacterial sample, breast milk, buffy coat, cells, cerebrospinal fluid, chromatin DNA, ejaculate, nucleic acids, plant-derived materials, RNA, saliva, semen, blood, serum, soil, synovial fluid, tears, tissue, urine, water, whole blood or plasma, and/or any combination and/or any fraction thereof. In an example, the sample can be a plasma sample, and the plasma sample can comprise DNA, RNA and/or protein. In another example, the sample can comprise a cell sample, and the cell sample can comprise DNA, RNA and/or protein. The sample can be a cellular sample or a cell-free sample (e.g., DNA and RNA in blood).

In some embodiments, a sample can be a mammalian sample. In some embodiments, a sample can be a human sample. In some embodiments, a sample can be a non-human animal sample. Non-limiting examples of a non-human sample include a cat sample, a dog sample, a goat sample, a guinea pig sample, a hamster sample, a mouse sample, a pig sample, a non-human primate sample (e.g., a gorilla sample, an ape sample, an orangutan sample, a lemur sample, or a baboon sample), a rat sample, a sheep sample, a cow sample, or a zebrafish sample.

The methods disclosed herein are generally useful for analyzing nucleic acids (e.g., circulating and/or cell-free DNA fragments). Nucleic acids may be derived from eukaryotic cells, prokaryotic cells, or non-cellular sources (e.g., viral particles). A person of skill in the art will appreciate that a nucleic acid can generally refer to a substance whose molecules consist of many nucleotides linked in a long chain. The nucleic acid can be a ribonucleic acid (RNA) or a deoxyribonucleic acid (DNA). The nucleic acid can comprise one or more secondary structures such as helices, loops, stem loops or hairpin loops, bulges, and junctions. Non-limiting examples of the nucleic acid include an artificial nucleic acid analog (e.g., a peptide nucleic acid, a morpholino oligomer, a locked nucleic acid, a glycol nucleic acid, or a threose nucleic acid), a modified nucleic acid (e.g., methylated nucleic acid), chromatin, cDNA, genomic DNA, plasmid DNA, messenger RNA (mRNA), ribosomal RNA (rRNA), transfer RNA (tRNA), small nuclear RNA (snRNA), small nucleolar RNA (snoRNA), guide RNA (gRNA), microRNA (miRNA), small interfering RNA (siRNA), short hairpin RNA (shRNA), and viral RNA. In some embodiments, nucleic acid can be double stranded or single stranded. In some embodiments, a sample can comprise a nucleic acid, and the nucleic acid can be intracellular. In some embodiments, a sample can comprise a nucleic acid, and the nucleic acid can be extracellular (e.g., cell-free). In some embodiments, a sample can comprise a nucleic acid (e.g., chromatin), and the nucleic acid can be fragmented.

Sample Processing

The present disclosure provides methods and systems for processing samples in assay tubes. Samples, such as nucleic acid samples, may be disposed in assay tubes and processed simultaneously or separately. The sample may be processed simultaneously but independent from one another. For example, a first sample in a first assay tube is subjected to different processing conditions then a second sample in a second assay tube. Alternatively, the first sample and the second sample may be subjected to the same or substantially the same processing conditions.

Samples may be processed using various assays. An assay may include nucleic acid amplification. For example, any type of nucleic acid amplification reaction may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, asymmetric amplification, rolling circle amplification, and multiple displacement amplification (MDA). In some embodiments, the amplified product may be DNA. In cases where a target RNA is amplified, DNA can be obtained by reverse transcription of the RNA and subsequent amplification of the DNA can be used to generate an amplified DNA product. The amplified DNA product may be indicative of the presence of the target RNA in the biological sample. In cases where DNA is amplified, various DNA amplification methods may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products. In some cases, nucleic acid amplification is isothermal. Non-limiting examples of isothermal nucleic acid amplification methods include helicase-dependent amplification, nicking enzyme amplification, recombinase polymerase amplification, loop-mediated isothermal amplification, and nucleic acid sequence based amplification.

Nucleic acid amplification reactions may be conducted in assay tubes in parallel. Nucleic acid amplification reactions may be conducted, for example, by including reagents necessary for each nucleic acid amplification reaction in a reaction vessel to obtain a reaction mixture and subjecting the reaction mixture to conditions necessary for each nucleic amplification reaction. Reverse transcription amplification and DNA amplification may be performed sequentially, such as, for example, performing reverse transcription amplification on RNA to generate complementary DNA (cDNA), and subsequently subjecting the cDNA to DNA amplification (e.g., PCR) to amplify the cDNA.

In some cases, a nucleic acid sample is amplified using reagents directed to a given target, such as, for example, a primer having sequence complementarity with a target sequence. After multiple heating and cooling cycles, any amplification products may be detected optically, such as using fluorophores. Fluorophore-labeled primers or hybridization probes and/or fluorescent dyes that bind to DNA maybe excited, and an emitted fluorescence detected. In some embodiments, methods the present disclosure include detecting fluorescence emission from a dye as well, and include calculating the ratio of fluorophore emission to dye emission. In some embodiments, a primer can comprise a fluorophore and a quencher. In some cases, a tertiary structure of an unbound primer is such a quencher is in close enough proximity to a fluorophore to prevent excitation of the fluorophore and/or the detection of an emission signal from the fluorophore.

In one embodiment, a fluorescent DNA dye, such as SYBR Green I, may be added to a mixture containing a target nucleic acid and at least one amplification primer. In some embodiments, an amplification primer may be a linear single-stranded oligonucleotide that is extendable by a DNA polymerase and that is labeled with a fluorophore that is excitable. Upon performing an amplification reaction, such as, e.g., a PCR reaction that includes annealing and extending the labeled primer, the fluorophore may be excited and an emission detected either during the amplification (real-time detection) or following completion of amplification (either an end-point detection at the conclusion of the amplification reaction or during a subsequent thermal analysis (melting curve)). Unincorporated primers may not fluoresce.

A wide range of fluorophores and/or dyes may be used in primers according to the present disclosure. Available fluorophores include coumarin, fluorescein, tetrachlorofluorescein, hexachlorofluorescein, *Lucifer* yellow, rhodamine, BODIPY, tetramethylrhodamine, Cy3, Cy5, Cy7, eosine, Texas red, SYBR Green I, SYBR Gold, 5-FAM (also called 5-carboxyfluorescein; also called Spiro(isobenzofuran-1 (3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluorosceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), Quasar-670 (Bioreseach Technologies), CalOrange (Bioresearch Technologies), Rox, as well as suitable derivatives thereof. Combination fluorophores such as fluorescein-rhodamine dimers, are also suitable. Fluorophores may be chosen to absorb and emit in the visible spectrum or outside the visible spectrum, such as in the ultraviolet or infrared ranges. Suitable quenchers can also include DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that may not fluoresce in the detection range when the probe is in the open conformation.

Allele-discriminating probes useful according to the invention also include probes that bind less effectively to a target-like sequence, as compared to a target sequence. The change in the level of fluorescence in the presence or absence of a target sequence compared to the change in the level of fluorescence in the presence or absence of a target-like sequence, can provide a measure of the effectiveness of binding of a probe to a target or target-like sequence.

DNA generated from reverse transcription of the RNA may be amplified to generate an amplified DNA product. Any suitable number of nucleic acid amplification reactions may be conducted. In some cases, at least 1, 2, 3, 4, 5, 6, 7, 8, 9, 10, 11, 12, 13, 14, 15, 16, 17, 18, 19, 20, or more nucleic acid amplification reactions are conducted.

For example, a target nucleic acid (e.g., target RNA, target DNA) may be extracted or released from a biological sample during heating phases of nucleic acid amplification. In the case of a target RNA, for example, the biological sample comprising the target RNA can be heated and the target RNA released from the biological sample. The released target RNA can begin reverse transcription (via reverse transcription amplification) to produce complementary DNA. The complementary DNA can then be amplified.

In any of the various aspects, primer sets directed to a target nucleic acid may be utilized to conduct nucleic acid amplification reaction. Primer sets generally comprise one or more primers. For example, a primer set may comprise at least 1, 2, 3, 4, 5, 6, 7, 8, 9, 10, or more primers. In some cases, a primer set or may comprise primers directed to different amplified products or different nucleic acid amplification reactions. For example, a primer set may comprise a first primer necessary to generate a first strand of nucleic acid product that is complementary to at least a portion of the target nucleic acid and a second primer complementary to the nucleic acid strand product necessary to generate a second strand of nucleic acid product that is complementary to at least a portion of the first strand of nucleic acid product.

In cases in which a plurality of assay tubes is used, the plurality of assay tube can include the same primers or primer sets, or different primers or primer sets. Each assay tube can be directed to a different target, or at least a subset of the assay tubes can be directed to the same target.

For example, a primer set may be directed to a target RNA. The primer set may comprise a first primer that can be used to generate a first strand of nucleic acid product that is complementary to at least a portion the target RNA. In the case of a reverse transcription reaction, the first strand of nucleic acid product may be DNA. The primer set may also comprise a second primer that can be used to generate a second strand of nucleic acid product that is complementary to at least a portion of the first strand of nucleic acid product. In the case of a reverse transcription reaction conducted with DNA amplification, the second strand of nucleic acid product may be a strand of nucleic acid (e.g., DNA) product that is complementary to a strand of DNA generated from an RNA template.

Where desired, any suitable number of primer sets may be used. For example, at least about 1, 2, 3, 4, 5, 6, 7, 8, 9, 10, or more primer sets may be used. Where multiple primer sets are used, one or more primer sets may each correspond to a particular nucleic acid amplification reaction or amplified product.

In some cases, a DNA polymerase is used. Any suitable DNA polymerase may be used, including commercially available DNA polymerases. A DNA polymerase generally refers to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products and derivatives thereof. For certain Hot Start Polymerase, a denaturation step at 94° C.-95° C. for 2 minutes to 10 minutes may be required, which may change the thermal profile based on different polymerases.

In some cases, a lysis agent is used. The lysis agent may be used to release a nucleic acid molecule, such DNA and/or RNA, from a biological particle, such as, for example, a cell or viral particle. Any suitable lysis agent may be used, including commercially available lysis agents. Non-limiting examples of lysis agents include Tris-HCl, EDTA, detergents (e.g., Triton X-100, SDS), lysozyme, glucolase, proteinase E, viral endolysins, exolysins zymolose, lyticase, proteinase K, endolysins and exolysins from bacteriophages, endolysins from bacteriophage PM2, endolysins from the *B. subtilis* bacteriophage PBSX, endolysins from *Lactobacillus* prophages Lj928, Lj965, bacteriophage 15 Phiadh, endolysin from the *Streptococcus pneumoniae* bacteriophage Cp-I, bifunctional peptidoglycan lysin of *Streptococcus agalactiae* bacteriophage B30, endolysins and exolysins from prophage bacteria, endolysins from *Listeria* bacteriophages, holin-endolysin, cell 20 lysis genes, and combinations thereof. In some cases a buffer may comprise a lysis agent (e.g., a lysis buffer). An example of a lysis buffer is sodium hydroxide (NaOH).

Sample Preparation Cartridges

Figure 2A:
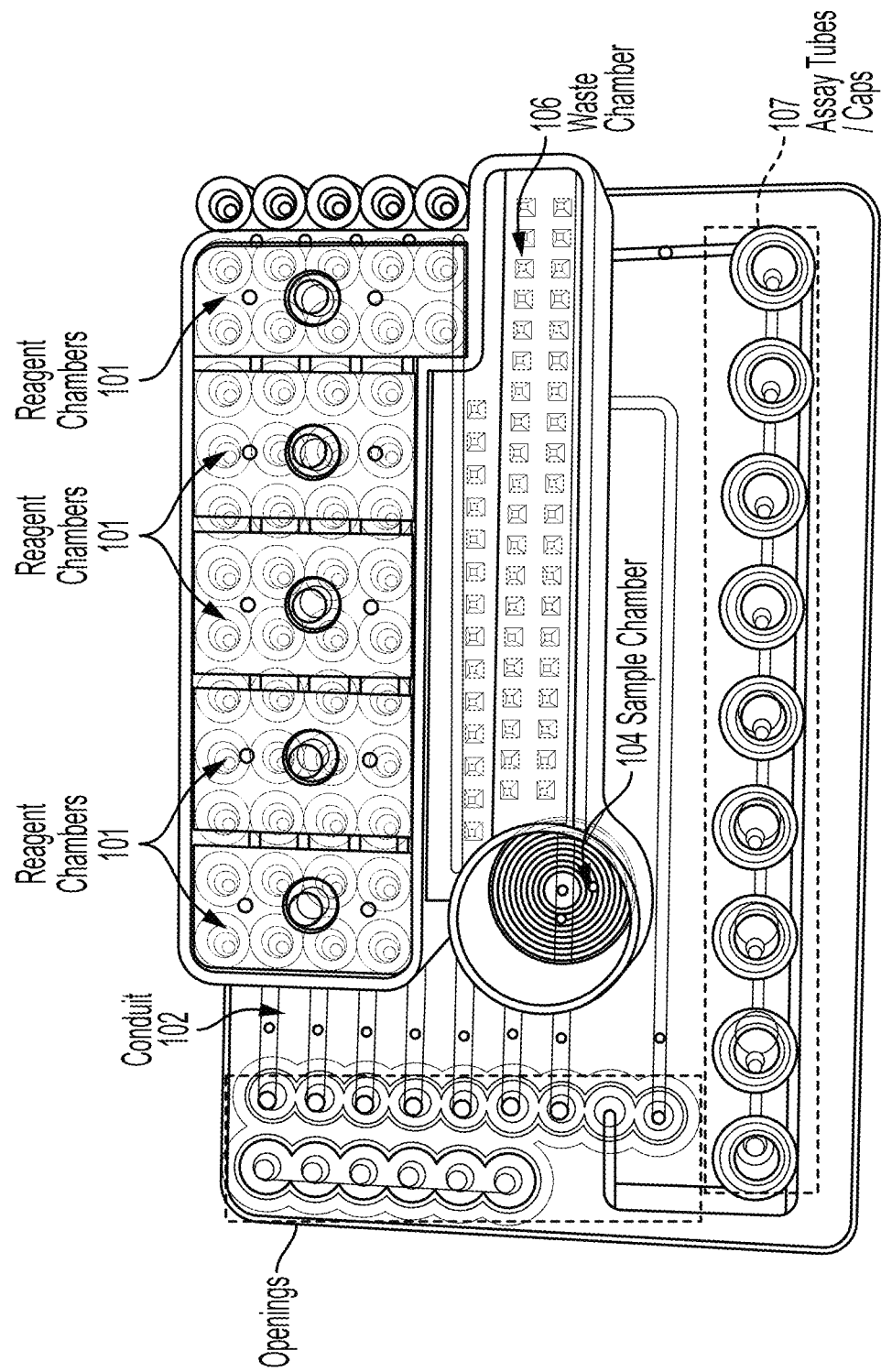
FIG. 2A shows a top view of an example sample preparation cartridge of the present disclosure.
Figure 2B:
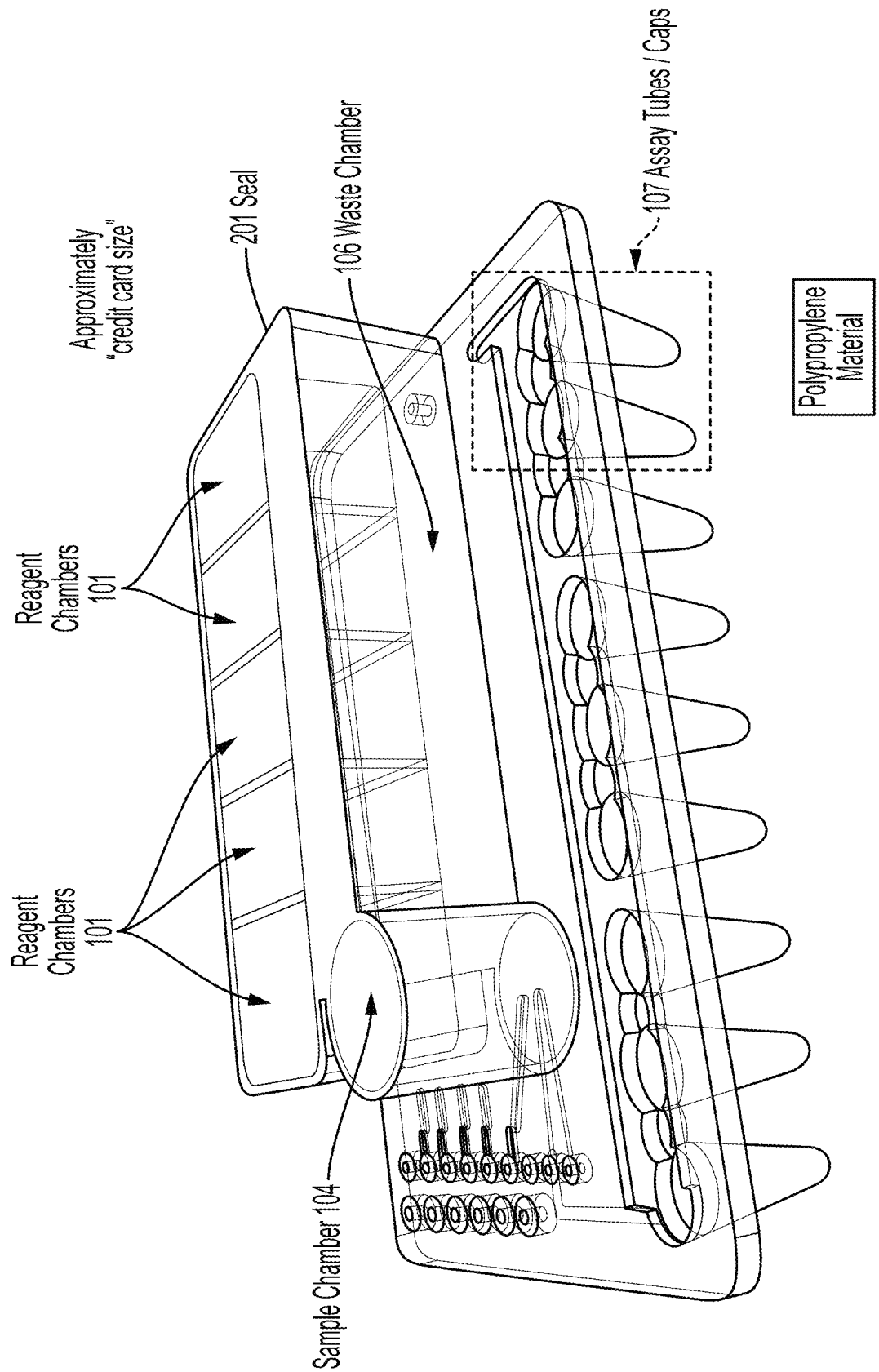
FIG. 2B shows a side view of an example sample preparation cartridge of the present disclosure.

The present disclosure provides sample preparation cartridges. Generally, sample preparation cartridges can comprise (i) one or more wells, each well containing a reagent necessary for processing the sample, (ii) a sample chamber for reacting the buffers with a sample, (iii) a chamber for depositing waste from the sample chamber, and (iv) one or more assay tubes for collecting a processed sample and performing an assay. Generally, the chambers and assay tubes can be connected by conduits (e.g., connections capable of transferring fluid from one chamber to another). Any of these conduits can comprise openings for connecting with a pump or valve to regulate flow of a liquid (e.g., a buffer or a sample) along the conduit. A top perspective view (FIG. 2A) and a side perspective view of example sample preparation cartridges are shown in FIG. 2.

Figure 10:
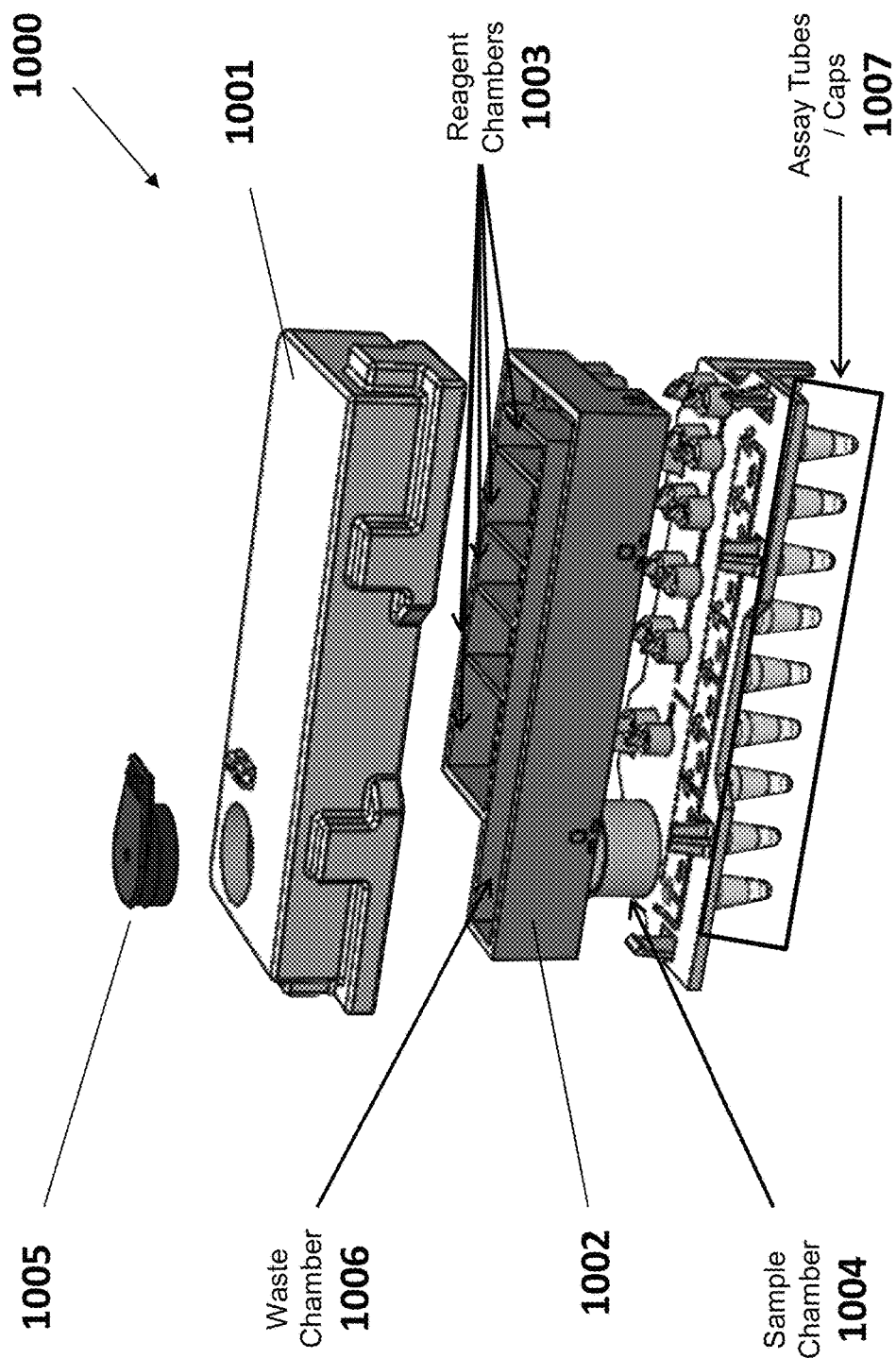
FIG. 10 shows an example of a sample preparation cartridge.

FIG. 10 shows an example of a sample preparation cartridge 1000. The sample preparation cartridge 1000 comprises a first manifold 1001 and a second manifold 1002. The second manifold 1002 comprises reagent chambers 1003 and a waste chamber 1006. The cartridge 1000 further comprises assay tubes 1007 and sample chamber 1004. The first manifold 1001 can be a shroud (e.g., a cover). The cartridge 1000 also comprises a cap 1005. The cartridge 1000 may be used with methods and systems of the present disclosure.

Figure 11:
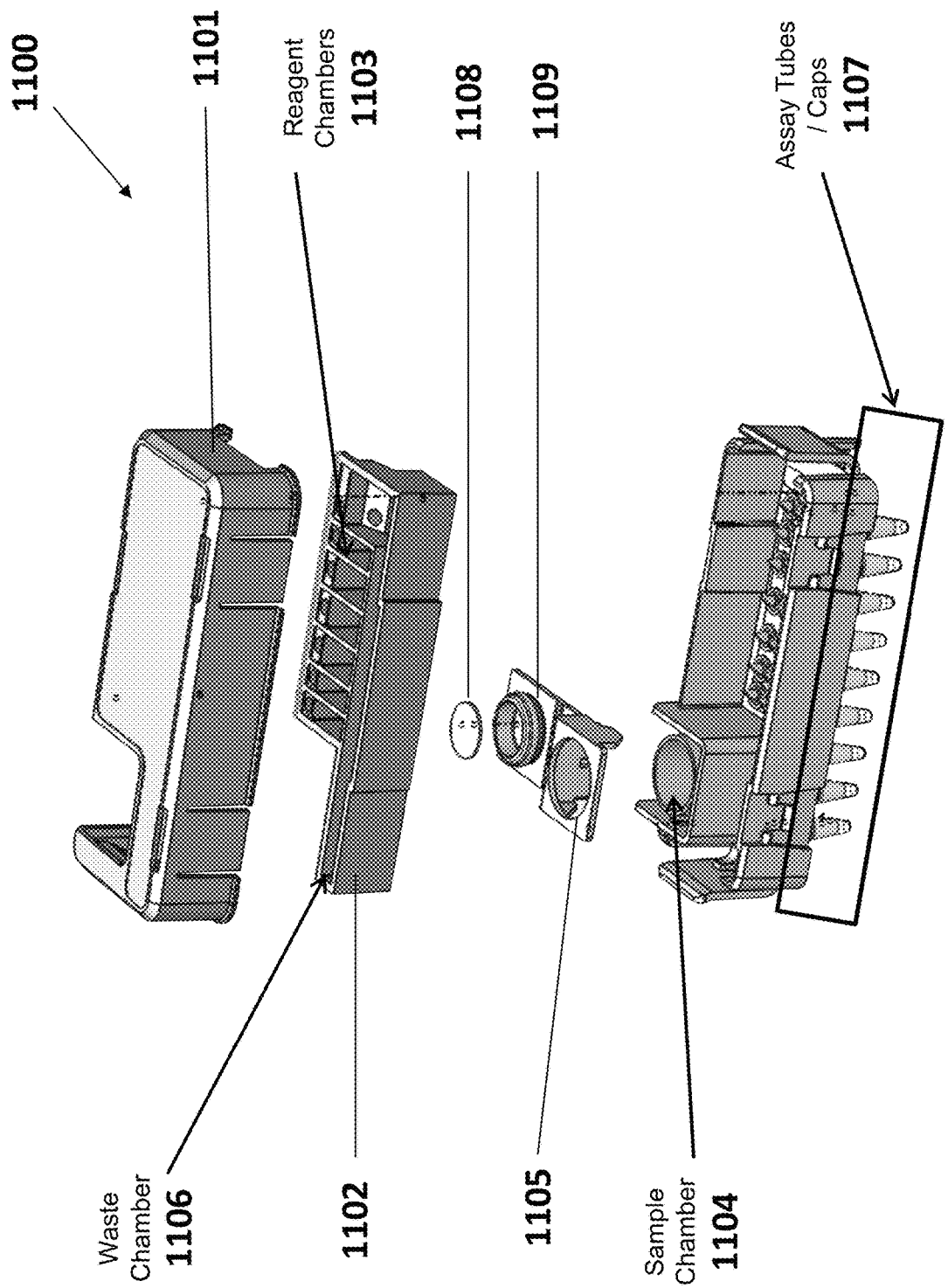
FIG. 11 shows an example of a sample preparation cartridge.

FIG. 11 shows another example of a sample preparation cartridge 1100. The sample preparation cartridge 1100 comprises a first manifold 1101 and a second manifold 1102. The second manifold 1102 comprises reagent chambers 1103 and a waste chamber 1106. The cartridge 1100 further comprises assay tubes 1107 and sample chamber 1104. The first manifold 1101 can be a shroud. The cartridge 1100 also comprises an additional cover piece 1105 for the sample chamber 1104. The additional cover piece 1105 further comprises a folding rubber cap 1109. The folding rubber cap 1109 further comprises a porous disc 1108 which can prevent fluids and aerosols from escaping but allow air to pass through the folding rubber cap.

Materials

Sample preparation cartridges may be formed of various materials. In some cases, the sample preparation cartridge may be formed of a single material (e.g., polypropylene). In some cases, the sample preparation cartridge may be formed of two or more materials. In some cases, materials that are useful for producing sample preparation cartridges include materials suitable for three-dimensional (3D) printing, injection molding, or other methods capable of forming a device with three-dimensional compartments and/or embedded conduits for fluid transfer between compartments. Non-limiting examples of materials that may be used to produce the sample preparation cartridge include polysiloxane, polyphosphazene, low-density polyethylene (ldpe), high-density polyethylene (hdpe), polypropylene (pp), polyvinyl chloride (pvc), polystyrene (ps), nylon, nylon 6, nylon 6,6, teflon (polytetrafluoroethylene), thermoplastic polyurethanes (tpu), polychlorotrifluoroethylene (pctfe), bakelite, kevlar, twaron, mylar, neoprene, nylon, nomex, orlon, rilsan, technora, teflon, ultem, vectran, viton, zylon, polyamides, polycarbonate, polyester, polyethylene, polyvinylidene chloride (pvdc), acrylonitrile butadiene styrene (abs), polyepoxide, polymethyl methacrylate, maleimide, polyetherimide, poly-lactic acid, furan, silicone, or polysulfone. In some cases, the sample preparation cartridge can be formed of a material comprising a thermoplastic, a thermosetting polymer, an amorphous plastic, a crystalline plastic, a conductive polymer, a biodegradable plastic, or a bioplastic. In one example, a sample preparation cartridge may be formed of a material comprising polypropylene. In another example, a sample preparation cartridge may be formed of a first material comprising polypropylene and a second material comprising polycarbonate.

Chambers

In some aspects, a sample preparation cartridge can comprise one or more chambers. Chambers may be useful for (i) storing buffers/reagents for sample processing, (ii) serially mixing a sample with a buffer or reagent to process a sample, and (iii) storing waste.

In some embodiments, a sample preparation cartridge can comprise 1 chamber. In some embodiments, a sample preparation cartridge can comprise a plurality of chambers. In some embodiments, a sample preparation cartridge can comprise 2 chambers, three chambers, 4 chambers, 5 chambers, 6 chambers, 7 chambers, 8 chambers, 9 chambers, 10 chambers, 15 chambers, 20 chambers, 25 chambers, 30 chambers, 35 chambers, 40 chambers, 45 chambers, 50 chambers, 100 chambers, or greater than 100 chambers. In one example, a sample preparation cartridge can comprise 5 chambers.

A size of a chamber (e.g., a sample chamber, a buffer chamber, or a waste chamber) can vary. In some embodiments, a chamber can hold at least about 0.1 milliliter (mL) of fluid. In some embodiments, a chamber can hold at least about 0.2 mL of fluid. In some embodiments, a chamber can hold at least about 0.3 mL of fluid. In some embodiments, a chamber can hold at least about 0.4 mL of fluid. In some embodiments, a chamber can hold at least about 0.5 mL of fluid. In some embodiments, a chamber can hold at least about 0.6 mL of fluid. In some embodiments, a chamber can hold at least about 0.7 mL of fluid. In some embodiments, a chamber can hold at least about 0.8 mL of fluid. In some embodiments, a chamber can hold at least about 0.9 mL of fluid. In some embodiments, a chamber can hold at least about 1 mL of fluid. In some embodiments, a chamber can hold at least about 1 mL, about 2 mL, about 3 mL, about 4 mL, about 5 mL, about 6 mL, about 7 mL, about 8 mL, about 9 mL, about 10 mL, or more of a fluid, such as a liquid.

In some embodiments, one or more of the chambers may be sealed. In some embodiments, the seal 201 may be removable or breakable (e.g., a user may break the seal on the chamber to add a sample to the chamber). The seal may be formed of a single material (e.g., aluminum) or a composition of two or more materials. In one example, the sample preparation cartridge may be formed of a material comprising polypropylene, and the seal may be formed of a material that comprises a tri-layer of an aluminum, adhesive layer and polypropylene layer. In some cases the seal material may allow a plastic syringe to penetrate the seal. The seal material may be a foil laminate. In some cases, a seal may adhere to the sample preparation cartridge at temperatures of a minimum of 10° C. up to and including 54° C., and maintain a seal for at least about 1 month, at least about 6 months, at least about 12 months, at least about 24 months, at least about 36 months, at least about 48 months or at least about 60 months. In some cases, a chamber may be permanently sealed. For example, a sample preparation cartridge can comprise a waste chamber, and the waste chamber may be permanently sealed.

In some embodiments, one or more of the chambers may be covered by a shroud. For example, as shown in FIG. 10 and FIG. 11, the manifold having one or more chambers is covered by a shroud.

In some embodiments, a chamber can comprise a reagent for performing an assay (e.g., a lysis buffer, a wash buffer, a drying agent, or an elution buffer). Non-limiting examples of buffers can comprise NP-40 lysis buffer, Radio Immunoprecipitation Assay (RIPA) lysis buffer, sodium dodecyl sulfate (SDS) lysis buffer, Ammonium-Chloride-Potassium (ACK) lysing buffer, volatile chemicals (e.g., acetone and ethanol), EDTA, Tris-HCl, and water.

In some embodiments, a chamber can comprise one or more buffers useful for analyzing a sample according to the Boom Method. In accordance with the Boom method, a biological sample is lysed and/or homogenized by mixing the biological sample with detergent in the presence of protein degrading enzymes. The chaotropic agents and silica or silica coated beads are mixed with the lysed biological sample. The chaotropic agents disrupt and denature the structure of nucleic acids by interfering with the macromolecular interactions mediated by non-covalent forces, such as hydrogen bonding, van der Waals forces, and hydrophobic interactions, for example. In the presence of the chaotropic agents, water is removed from the phosphate groups of the nucleic acids, exposing them and allowing hydrophobic bonding to the silica, such as silica or silica coated beads. Protein, cellular debris, and other substances in the biological samples do not bond to the silica and are retained in the solution. The silica beads are washed several times to remove non-nucleic acid materials, such as proteins, lipids, cellular constituents, including cellular molecules, and other substances found in biological samples. Silica coated magnetic beads may be used to assist in the separation of the nucleic acids bound to the silica coating from the solution, via a magnetic field or magnet. The nucleic acids are then eluted from the silica or silica coated beads into a buffer by decreasing the concentration of the chaotropic agents. The elution buffer may be pure water or Tris-EDTA ("TE") buffer, for example.

Figure 3:
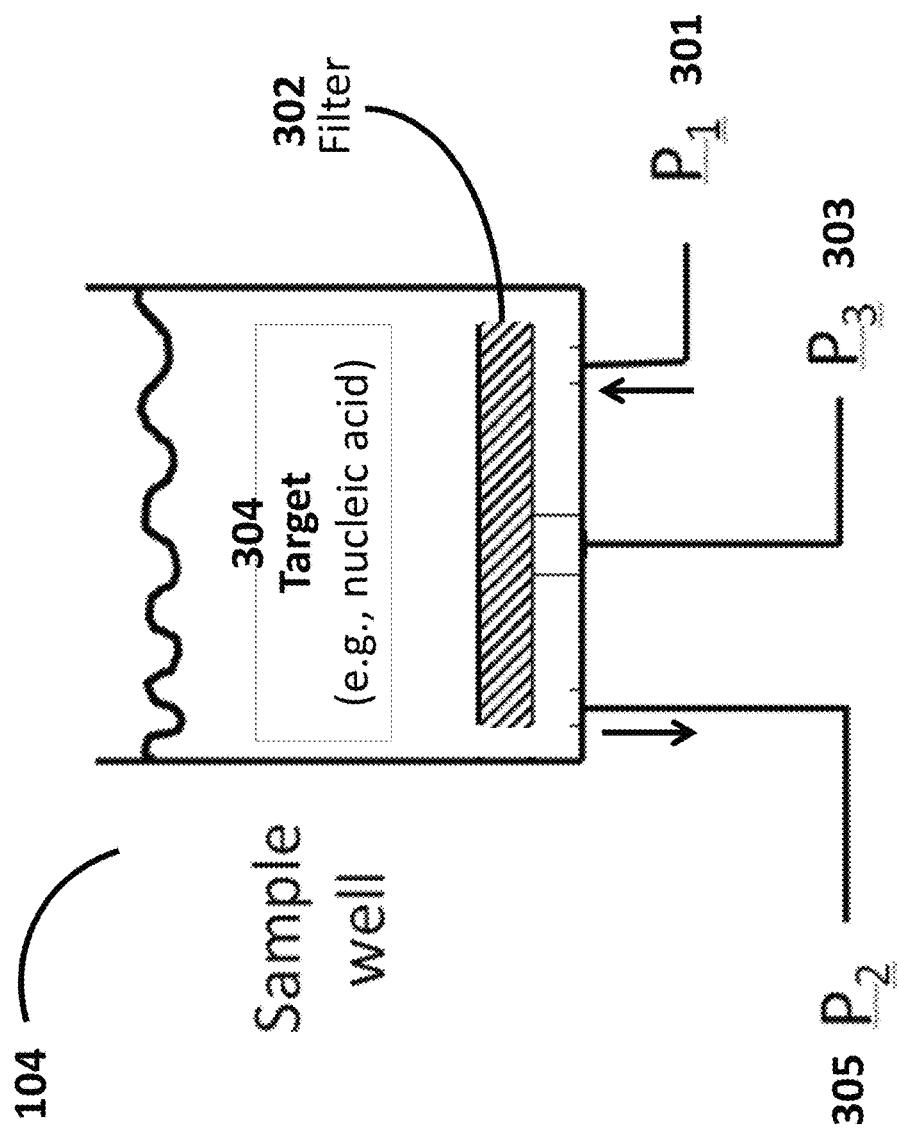
FIG. 3 shows a cross-sectional view of a sample chamber of a sample preparation cartridge.

In some aspects, the sample preparation cartridge can comprise a sample chamber. Generally, a sample may be added to the sample chamber, after which buffers are serially added to the sample chamber to process the sample. A sample chamber may be fluidly connected to a buffer chamber (e.g., via a conduit) such that a pump disposed along the conduit can transfer the buffer automatically to the sample chamber. After mixing the sample with a given buffer, the mixture is pulled through a filter located within the sample chamber, the filter configured to capture a target (e.g., a nucleic acid) within the sample. An elution buffer may be added to the sample chamber to release the target from the filter. The sample chamber and filter can be configured such that fluid can be quickly pumped into the sample chamber (e.g., around the filter) and pumped out of the sample chamber through the filter (e.g., to capture a target in the sample). In some cases the filter may be movable (e.g., shift between a first position and a second position) to allow the fluid to quickly enter the sample chamber. In some cases, the filter may be capable of bending or translocating, e.g., as described in U.S. Pat. No. 9,926,553, which is entirely incorporated herein by reference. An example sample chamber is shown in FIG. 3. Reagents (e.g., lysis buffer, wash buffer) may be pump into the sample chamber 104 using pressure generated from a pump 301. In a filling stage (e.g., when reagent is being added to the sample chamber), a reagent may enter the sample chamber by flowing around a filter 302. This can reduce the resistance experienced by the pump, and allow the reagent to fill the sample chamber more quickly. After the reagent has mixed with the sample, an additional pump 303 may be used to transfer the mixture through the filter configured to capture a target (e.g., nucleic acid) 304 in the sample to the waste chamber. After the target is processed and bound to the filter, an elution buffer may be pumped into the sample chamber to capture the target from the filter; a third pump 305 may be used to transfer the sample to an assay tube for further analysis. In some embodiments, the sample chamber is covered by a cap. In some embodiments, the sample chamber is covered by a folding rubber cap. In some embodiments, the folding rubber cap comprises a porous disc. The porous disc can prevent fluids and aerosols from escaping but allow air to pass through the cap.

In some embodiments, it may be beneficial to heat the sample. Accordingly, a heater may be provided adjacent to the sample chamber (e.g., below the sample chamber) to provide heat to the sample and/or the sample chamber. For example, prior to extracting the target from the filter, the sample chamber and/or filter may be washed with a volatile solvent (e.g., ethanol or acetone). Subsequently, a heater may be used to apply heat to the sample and/or sample chamber to evaporate any remaining volatile solvent. It is also possible to improve both product yield as well as specificity of PCR by preparing a sample or a reaction mixture at increased temperatures (e.g., a temperature greater than an annealing temperature of a primer). Pre-amplification heating may promote annealing of the primer to a target nucleic acid, subsequent extension, as well as minimize the formation of primer-dimers or primer self-annealing. A pre-amplification heating step may be particularly useful for processing samples with low nucleic acid content, as the sample may be split into two or more assay tubes and pre-amplification heating of the sample could increase product yield in each assay tube. Accordingly, a pre-amplification heating step may be implemented in any of the embodiments of the present disclosure. For example, prior to transferring a sample from the sample chamber to one or more assay tubes, a heater may be used to heat the sample. In another example, lysis buffer may be pumped into the sample chamber, and subsequently heated. Heat can help denature the sample, reduce the formation of precipitates from the sample, or help return precipitated solids back into the sample solution. Using heat to homogenize the solution (e.g., reduce the precipitation of solids from the sample) can reduce buildup and clogs within a conduit as the sample is being transferred through the conduit. A heating step may be performed at any given temperature for any period of time. In some embodiments, a sample may be heated at 70° C. In some embodiments, a sample may be heated at 70° C. for a period of 10 minutes. In some embodiments, a sample may be heated at 70° C. indefinitely until the sample is transferred to one or more assay tubes for further processing. In some embodiments, a sample may be heated at a single temperature. In some embodiments, a sample may be heated over a range of temperatures (e.g., a range of increasing temperatures, or a range of decreasing temperatures). The heater may further comprise a spring-loaded plate. The spring-loaded plate can provide improved thermal contact with the sample chamber compared with a heater without such spring-loaded plate.

In general, a filter can comprise any material capable of capturing a target (e.g., a nucleic acid) from a sample. A filter may be organic or inorganic; may be metal (e.g., copper or silver) or non-metal; may be a polymer or may not be a polymer; may be conducting, semiconducting or nonconducting (insulating); may be reflecting or nonreflecting; may be porous or nonporous; etc. A filter as described above can be formed of any suitable material, including metals, metal oxides, semiconductors, polymers (particularly organic polymers in any suitable form including woven, nonwoven, molded, extruded, cast, etc.), silicon, silicon oxide, and composites thereof. A number of materials (e.g., polymers) suitable for use as filters in the instant invention may be used. Suitable materials for use as filters include, but are not limited to, polycarbonate, gold, silicon, silicon oxide, silicon oxynitride, indium, tantalum oxide, niobium oxide, titanium, titanium oxide, platinum, iridium, indium tin oxide, diamond or diamond-like film, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polyacrylonitrile (PAN), polyacrylate, polycarbonate, polybutylene terephthalate (PBT), poly(ethylene) (PE) (including low density, linear low density, high density, cross-linked and ultra-high molecular weight grades), poly(propylene) (PP), cis and trans isomers of poly(butadiene) (PB), cis and trans isomers of poly(isoprene), polyethylene terephthalate) (PET), polypropylene homopolymer, polypropylene copolymers, polystyrene (PS) (including general purpose and high impact grades), polycarbonate (PC), poly(epsilon-caprolactone) (PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinyl alcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), styrene maleic anhydride (SMA), metal oxides, glass, glass wool, silicon oxide or other inorganic or semiconductor material (e.g., silicon nitride), compound semiconductors (e.g., gallium arsenide, and indium gallium arsenide), and combinations thereof.

Examples of filters include polypropylene, polystyrene, polyethylene, dextran, nylon, amylases, glass, natural and modified celluloses (e.g., nitrocellulose), polyacrylamides, agaroses and magnetite. In some instances, the filter can be silica or glass because of its great chemical resistance against solvents, its mechanical stability, its low intrinsic fluorescence properties, and its flexibility of being readily functionalized. In an example, the filter is formed of silicon oxide (e.g., glass).

A filter material may be modified with one or more different layers of compounds or coatings that serve to modify the properties of the surface in a desirable manner. For example, a filter may further comprise a coating material on the whole or a portion of the surface of the filter. For example, the coating material can be nitrocellulose, silane, thiol, disulfide, or a polymer. When the material is a thiol, the filter may comprise a gold-coated surface and/or the thiol comprises hydrophobic and hydrophilic moieties. When the coating material is a silane, the filter comprises glass and the silane may present terminal moieties including, for example, hydroxyl, carboxyl, phosphate, glycidoxy, sulfonate, isocyanato, thiol, or amino groups. In an alternative embodiment, the coating material may be a derivatized monolayer or multilayer having covalently bonded linker moieties. For example, the monolayer coating may have thiol (e.g., a thioalkyl selected from the group consisting of a thioalkyl acid (e.g., 16-mercaptohexadecanoic acid), thioalkyl alcohol, thioalkyl amine, and halogen containing thioalkyl compound), disulfide or silane groups that produce a chemical or physicochemical bonding to the filter. The attachment of the monolayer to the filter may also be achieved by non-covalent interactions or by covalent reactions.

After attachment to the filter, the coating may comprise at least one functional group. Examples of functional groups on the monolayer coating include, but are not limited to, carboxyl, isocyanate, halogen, amine or hydroxyl groups. In one embodiment, these reactive functional groups on the coating may be activated by standard chemical techniques to corresponding activated functional groups on the monolayer coating (e.g., conversion of carboxyl groups to anhydrides or acid halides, etc.). Examples of activated functional groups of the coating on the filter for covalent coupling to terminal amino groups include anhydrides, N-hydroxysuccinimide esters or other common activated esters or acid halides, Examples of activated functional groups of the coating on the filter include anhydride derivatives for coupling with a terminal hydroxyl group; hydrazine derivatives for coupling onto oxidized sugar residues of the linker compound; or maleimide derivatives for covalent attachment to thiol groups of the linker compound. To produce a derivatized coating, at least one terminal carboxyl group on the coating can be activated to an anhydride group and then reacted, for example, with a linker compound. Alternatively, the functional groups on the coating may be reacted with a linker having activated functional groups (e.g., N-hydroxysuccinimide esters, acid halides, anhydrides, and isocyanates) for covalent coupling to reactive amino groups on the coating.

In some embodiments, the sample preparation cartridge can also comprise a waste chamber. In some cases, a waste chamber may be fluidly connected to a sample chamber (e.g., via a conduit) such that the sample may be drawn through a filter in the sample chamber, and transferred the waste to the waste chamber.

Conduits

Any compartment of the sample preparation cartridge (e.g., a chamber or an assay tube) may be fluidly connected to one or more other compartments of the sample preparation cartridge by one or more conduits. The sample preparation cartridge may comprise 2, 3, 4, 5, 6, 7, 8, 9, 10, 11, 12, 13, 14, 15, 16, or more conduits. Generally, a conduit may be used to connect two compartments in order to allow a sample or reagent to pass between the two compartments. For example, the sample chamber may be fluidly connected to the waste chamber to allow fluid to be pumped from the sample chamber to the waste chamber.

The structure of the sample preparation cartridges described herein can comprise an aggregation of two or more separate layers which when appropriately mated or joined together, form the conduits described herein. For example, a bottom surface of a top layer and a top surface of a bottom layer can each comprise a trench (e.g., a channel or a groove) that, when mated together, form a conduit. Typically, the sample preparation cartridges described herein will comprise a top portion, a bottom portion, and an interior portion, wherein the interior portion substantially defines the conduits of the cartridge. For example, the body structure is fabricated from at least two substrate layers that are mated together to define the conduit networks of the cartridge, e.g., the interior portion. In some cases, the top portion of the cartridge can comprise the chambers (e.g., sample chambers, buffer chamber, and waste chamber). In some cases, the bottom portion of the cartridge comprises one or more adapters or caps to which an assay tube may be coupled.

A variety of materials may be employed to fabricate the top and/or bottom layer of the sample preparation cartridge, as described above. In some cases, materials can be selected based upon their compatibility with various fabrication techniques, e.g., photolithography, wet chemical etching, laser ablation, air abrasion techniques, LIGA, reactive ion etching (RIE), injection molding, embossing, and other techniques. The materials can also generally be selected for their compatibility with the full range of conditions to which the sample preparation cartridges may be exposed, including extremes of pH, temperature, salt concentration, and application of electric fields. Accordingly, in some aspects, the material may include, e.g., silica based substrates, such as glass, quartz, silicon or polysilicon. In the case of semi conductive materials, it will often be desirable to provide an insulating coating or layer, e.g., silicon oxide, over the material, and particularly in those applications where electric fields are to be applied to the cartridge or its contents.

In some aspects, the materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates may be readily manufactured using fabrication techniques; using molding techniques, such as injection molding, embossing or stamping; or by polymerizing the polymeric precursor material within the mold. Such polymeric materials are for their ease of manufacture, low cost and disposability, as well as their general inertness to most extreme reaction conditions. Again, these polymeric materials may include treated surfaces, e.g., derivatized or coated surfaces, to enhance their utility in the sample preparation cartridge, e.g., provide enhanced fluid direction.

Sample preparation cartridges may be used in a variety of applications, including, e.g., the performance of high throughput screening assays in drug discovery, immunoassays, diagnostics, nucleic acid analysis, including genetic analysis, and the like. As such, the cartridges described herein, will often include one or more conduit openings. A conduit opening can generally refer to any opening through which a conduit, and the corresponding chamber to which the conduit is connected, may be accessed. Conduit openings may be useful for a variety of reasons. Firstly, conduit openings can allow for the insertion of a pump or valve along the conduit. This is particularly useful for preparing disposable sample preparation cartridges, as described below. Conduit openings in the sample preparation cartridge allow the cartridge to dock with the re-useable sample preparation device (e.g., the re-useable device comprising pumps, valves, and/or electronic components). Conduit openings in the sample preparation cartridge allow for the cartridge to be produced without more expensive components.

Secondly, conduit openings can allow for different chambers of the sample preparation cartridge to be fluidly connected, via their respective conduits, depending on the assay being performed. In some embodiments, a sample preparation cartridge can comprise multiple sets of reagents, each set of reagents for processing a sample for a particular assay to be performed. For example, a sample preparation device may be configured such that, upon docking the sample preparation cartridge to the sample preparation device, the reagents in chambers 1 through 5 are serially transferred to the sample chamber. In another example, a sample preparation device may be configured such that, upon docking the sample preparation cartridge to the sample preparation device, the reagents in chambers 6 through 10 are serially transferred to the sample chamber. In yet another example, a sample preparation device may be configured such that, upon docking the sample preparation cartridge to the sample preparation device, the reagent in chamber 1 is mixed with the reagent in chamber 2, and subsequently the mixture of the two reagents is serially transferred to the sample chamber.

In some embodiments, a sample preparation cartridge can comprise a separate conduit that is fluidly connected to each chamber on the cartridge. In some embodiments, a sample preparation cartridge can comprise two or more chambers that are connected to a common or primary conduit via separate secondary conduits. For example, a first conduit fluidly connected to a first chamber and a second conduit fluidly connected to a second chamber may both fluidly connect to a primary conduit. Any number of secondary conduits, each of which may be fluidly connected to one a chamber or assay tube, maybe fluidly connected to a primary conduit. In some cases where multiple secondary conduits are fluidly connected to a single primary conduit, valves may be used to restrict flow to one or more specific secondary conduits.

Multiple sample introduction ports or sample chambers are contemplated for the parallel or serial introduction and analysis of multiple samples. Alternatively, cartridges may be coupled to a sample introduction port, e.g., a pipette, which serially introduces multiple samples into the cartridge for analysis.

Assay Tubes and Caps

Figure 8:
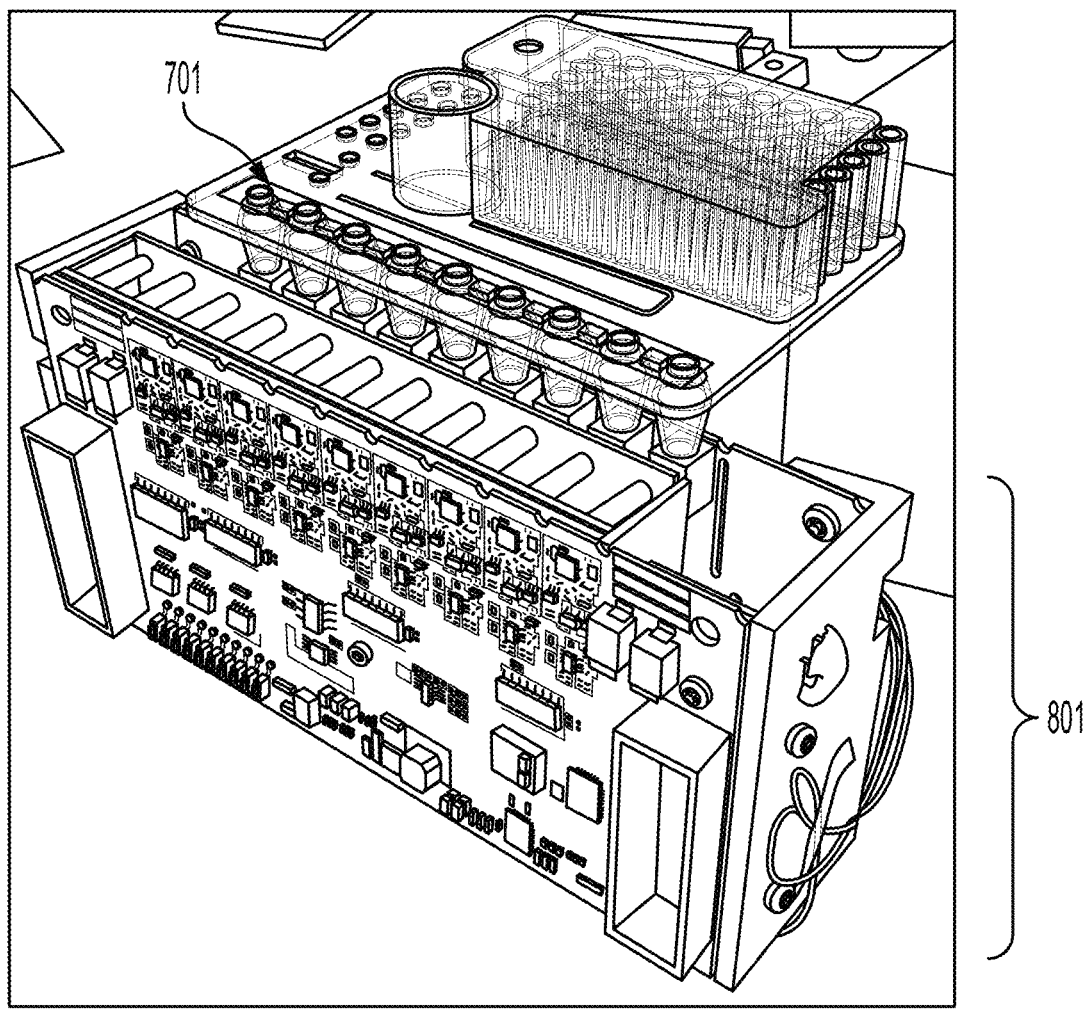
FIG. 8 shows a sample preparation cartridge with assay tubes docked to an analytic device capable of performing an assay (e.g., polymerase chain reaction and/or detection of a target nucleic acid) on the sample in the assay tube.

In some embodiments, a sample preparation cartridge of the present disclosure can comprise one or more assay tubes, each having an assay tube cap, fluidly connected to the sample chamber (see, e.g., FIG. 4). It should be understood that an assay tube may be interchanged with a chamber in any embodiment of the present disclosure. Generally, following processing of the sample, an elution buffer may be added to the sample chamber to extract the target (e.g., nucleic acid) from the filter, and transfer the target to the assay tube. Assay tubes may be transparent, such that they are capable of transmitting an optical signal from the sample in the assay tube, the optical signal capable of being detected by an analytic device 801 (see, e.g., FIG. 8), as described, for example, in U.S. Patent Publication No. 2017/0183713, which is entirely incorporated herein by reference. Various PCR tubes may be used. For example, the assay tube may be a 0.1 ml or 0.2 ml PCR tube, or other thin-walled commercially available PCR tubes. Suitable PCR tubes may be obtained from Phenix Research Products, Candler, North Carolina, BIOplastics, for example. In some embodiments, an assay tube cap may be removably coupled (e.g., separable) to the sample preparation cartridge; an assay tube may be coupled directly to the cap. For example, the sample preparation cartridge may be removably attached (e.g., by a perforation) to a strip of assay tube caps to which assay tubes may be press-fit or snap fit. Having one or more assay tube caps removably attached to the sample preparation cartridge can be advantageous as the assay tubes (containing a sample) and caps can be quickly separated from the sample preparation cartridge and loaded into an analytic device (e.g., a thermal cycler).

Figure 13:
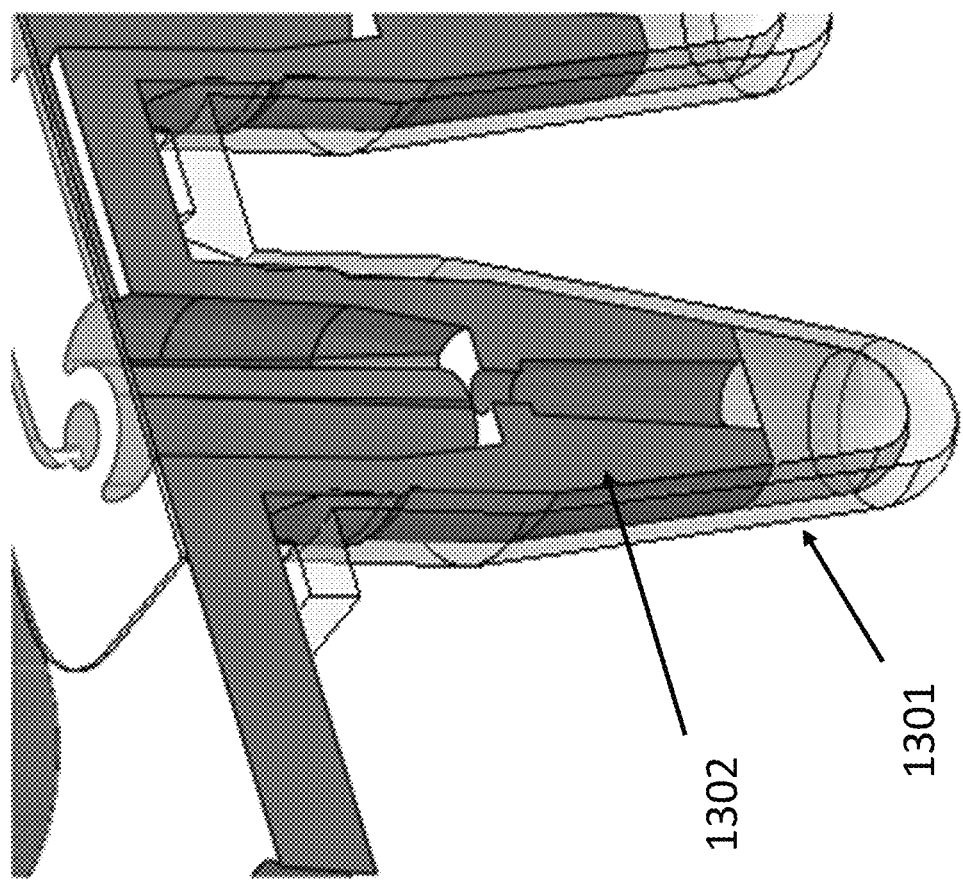
FIG. 13 shows an example cross-sectional view of an assay tube and a cap.

In some embodiments, an assay tube cap 401 can comprise one or more conduits 402 through which (i) a sample 403 may be transferred into the assay tube, and/or (ii) a pressure 404 may be applied (e.g., to draw fluid into the assay tube). Generally, a conduit may pass through the assay tube cap, thereby providing a fluid connection between the assay tube and the conduit (e.g., a conduit extending from a sample chamber). An example cross-sectional view of the assay tube (1301) and cap (1302) is shown in FIG. 13.

An assay tube cap can have one or more first conduits passing through the cap to supply the assay tube with a reagent or sample. In some embodiments, an end of the conduit can have a tip or nozzle 405, to control the flow of a reagent or sample out of the conduit. A person having skill in the art will appreciate that a variety of different aspects of the flow may be controlled. Non-limiting examples include the flow rate, the type of flow (e.g., laminar or turbulent), and a size of droplet formed. Two concerns in liquid delivery through nozzles include (i) how to eject a droplet cleanly so that a drop is not left hanging on the end of the nozzle, and (ii) how to keep the contents of the assay tube from splashing when the stream of liquid is delivered into the assay tube. Further, the ejection velocity of the liquid from the nozzle must be sufficient to induce mixing between the first and second delivered liquid in the reaction chamber. Very small droplets can be ejected cleanly at high ejection velocities, but do not have sufficient kinetic energy to overcome the surface tension of the liquid already in the well to cause mixing. In contrast, larger droplets also eject cleanly at high ejection velocities, but tend to splash the contents into adjacent wells. At lower ejection velocities, the liquids tend to leave the last drop hanging from the nozzle tip, which is also a function of the cross-sectional area of the tip. Moreover, the flow rate of liquids through the conduit varies directly with the delivery pressure and inversely with the length of the conduit and inversely with the diameter. All these variables must be taken into consideration when developing delivery pressure and tip configurations, as well as the materials of construction, so that the liquids can be expelled cleanly without leaving a residual drop of liquid hanging from the nozzle tip. In some cases, the nozzle or tip may be used to increase a cross-sectional area of the conduit. In some cases, the cross-sectional area of the conduit may gradually increase along a length of the nozzle or tip. In some cases, the nozzle or tip may be used to decrease a cross-sectional area of the conduit. In some cases, the cross-sectional area of the conduit may gradually decrease along a length of the nozzle or tip. The nozzle can be any shape. In some embodiments, a nozzle may be conical in shape. In some cases, the nozzle may be cylindrical in shape. In some cases the nozzle may be hemispherical in shape. The shape of the nozzle may be selected based on depending on the liquid, it may be more beneficial to dispense it in a continuous stream, a series of pulses or in droplet form.

In some cases, an assay tube cap can have one or more second conduits 406 passing through the cap. These one or more second conduits can be coupled to a pump, and used to generate a draw pressure through the assay tube to draw a sample or reagent from a chamber (e.g., the sample chamber) to the assay tube. It is contemplated that a hydrophobic and/or porous material 407 may be use to prevent liquid from entering the second conduit as the sample fills the assay tube. For example, a molecular sieve (e.g., a material permeable to a gas but not liquid) may be positioned at an end of the second conduit such that a draw pressure can be applied through the sieve to draw a sample into the assay tube. The molecular sieve may be permeable to one or more gases, such as air. However, as the sample fills the assay tube (see, e.g., FIG. 4B), the molecular sieve may prevent the sample from flowing into the second conduit. A molecular sieve used in any embodiment of the present disclosure can be a microporous molecular sieve, a mesoporous molecular sieve, or a macroporous molecular sieve. Non-limiting examples of molecular sieves include zeolites, aluminosilicate materials, porous glass, active carbon, clay, monmorillonite, halloysite, silicon dioxide, and silica. In some cases, the molecular sieve is a filter, for example, a pipette tip filter. The filter can self-seal upon contacting a liquid. The filter material may be hydrophobic, for example, polytetrafluoroethylene and polyethylene. In some cases, the filter have a small pore size, for example, from 10 to 12 μm, from 12 to 15 μm, from 15 to 20 μm, or from 20 to 25 μm.

Figure 5A:
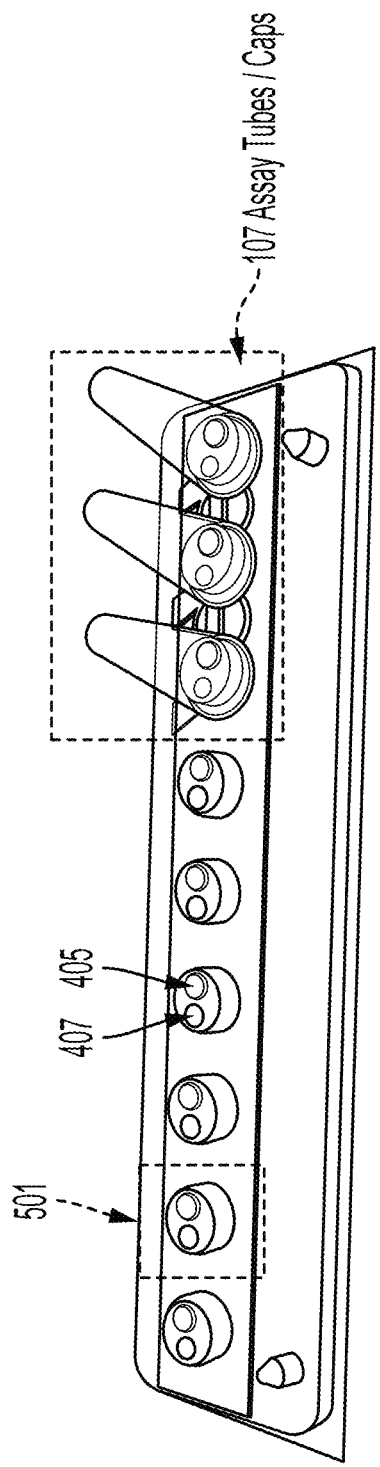
FIG. 5A shows strips of assay tube caps having various lengths (e.g., along a longitudinal axis of the assay tube), each cap comprising a channel through which a sample may be drawn into the assay tube.
Figure 5B:
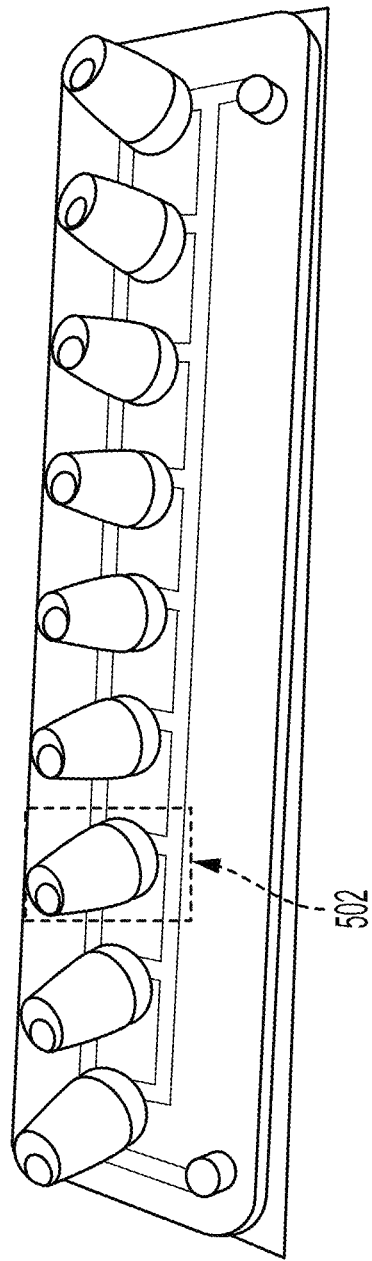
FIG. 5B shows strips of assay tube caps having various lengths (e.g., along a longitudinal axis of the assay tube), each cap comprising a channel through which sample is drawn into the assay tube.

In some embodiments, two or more caps can have varying thicknesses causing the cap to extend into an assay tube, thereby affecting the maximum working volume of the assay tube. Example assay tube caps and assay tubes are shown in FIG. 5A-B. FIG. 5A shows assay tube caps having a lesser thickness 501 as compared to assay tube caps having a greater thickness 502 shown in FIG. 5B. Generally, the greater the thickness of a cap (e.g., causing the cap to extend further into the assay tube) the lower the maximum working volume of the assay tube. This can be beneficial for small volume samples. In some cases, the thickness of the assay tube cap may be at least about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.5 mm, about 3 mm, about 4 mm, about 5 mm, about 6 mm, about 7 mm, about 8 mm, about 9 mm, about 10 mm or greater than about 10 mm. In some cases, the working volume of an assay tube may not be reduced. In some cases, the working volume of the assay tube may be reduced by at least about 1% about 2%, about 3% about 4%, about 5%, about 10%, about 15%, about 20%, about 25%, about 50%, about 75% or more than about 75%. Increasing the thickness of the cap reduces the distance between the bottom of the assay tube and the end of the conduit through which a sample is deposited into the assay tube; this can affect the mixing of the sample as a droplet falls into liquid already in the assay tube, as described above.

Sample Preparation Devices

Figure 7:
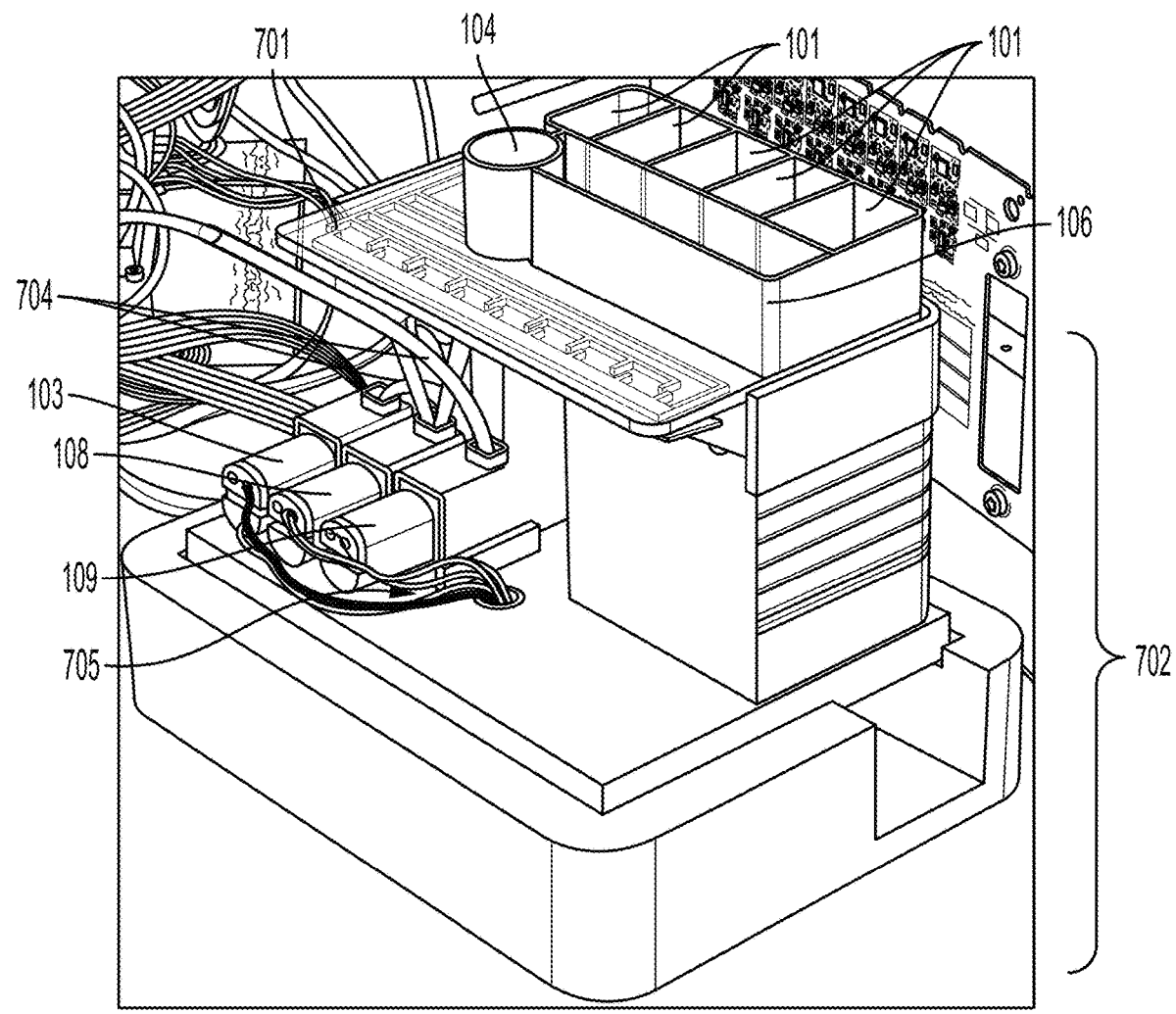
FIG. 7 shows a sample preparation cartridge docked to an automated sample preparation device.
Figure 9:
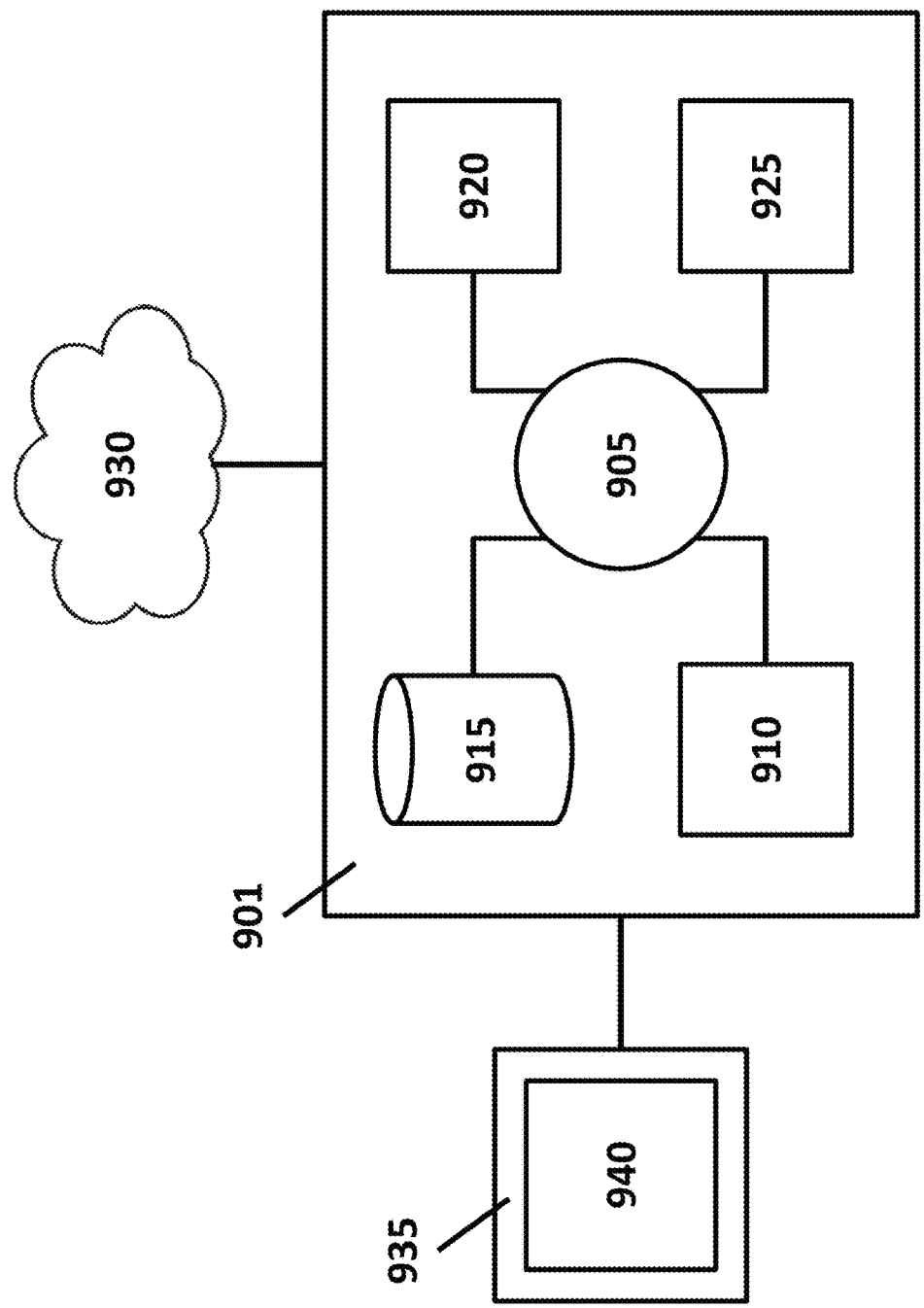
FIG. 9 shows a computer control system that is programmed or otherwise configured to implement methods provided herein.

The sample preparation cartridge can be one component of a larger system which may comprise a sample preparation device for transferring fluids from one chamber to another chamber or an assay tube, and a computer based interface for controlling the device and/or interpretation of the data derived from the device. The sample preparation device can include a variety of mechanical elements (e.g., pumps and/or valves), and other computer-controlled systems. An example system is shown in FIG. 7. The sample preparation cartridge includes a housing comprising various chambers. A sample preparation cartridge 701, as shown in FIG. 2A, is docked to a sample preparation device 702 having pumps 103, 108, and 109 and/or valves (not shown) to control the transfer of fluid between two or more chambers, including a reagent chamber 101, a sample chamber 104, and a waste chamber 106 (e.g., from a reagent chamber to a sample chamber). Once docked, conduits leading from one or more sample chambers become fluidly connected 704 (e.g., via tubing or channels) to one or more pumps and/or valves, thereby allowing the pumps and/or valves to control the flow of fluid from one chamber to another. The pumps and/or valves may be controlled wirelessly or using an electrical connection 705 by one or more computer control systems, as shown in FIG. 9.

The sample preparation cartridge may include information stored in a radiofrequency identification (RFID) unit or memory. The information may include a barcode that may uniquely identify the sample being processed, routines for processing the sample, or information about a user of the cartridge. Alternatively, the sample preparation cartridge may not include any RFID unit or memory. In some embodiments, the sample preparation may include a printed barcode or alpha-numeric code that may uniquely identify the sample being processed, routines for processing the sample, or information about a user of the cartridge.

The sample preparation device may comprise one or more fluid flow units. The fluid flow unit can be in fluid communication with a conduit and can be configured to subject a reagent to flow from a chamber (or well) to another chamber (or well). The sample preparation device may comprise at least 1, at least 2, at least 3, at least 4, at least 5, at least 6, at least 7, at least 8, at least 9, at least 10, at least 20, at least 30, at least 40, or more fluid flow units. The fluid flow unit can comprise a pump or a compressor. In some cases, the fluid flow unit is a pump or a compressor. In some cases, the fluid flow unit can comprise at least 1, at least 2, at least 3, at least 4, at least 5, at least 6, at least 7, at least 8, at least 9, at least 10, at least 20, at least 30, at least 40, or more pumps or compressors.

Pumps may be employed to generate pressure within the conduits to draw fluid from one chamber to another chamber or to generate bubbles within a chamber to induce mixing of a liquid in the chamber. A pump can be disposed along a conduit, or along tubing connecting one conduit opening to another. The pressure applied by the pump can be intermittent (e.g., a peristaltic pump) or continuous (e.g., a dynamic pump or velocity pump). A variety of devices may be employed. Non-limiting examples of pumps that may be used include a positive displacement pump, a gear pump, a screw pump, a rotary vane pump, a reciprocating pump, a plunger pump, a diaphragm pump, a piston pump, a rotary lobe pump, a progressive cavity pump, a rotary gear pump, a piston pump, a hydraulic pump, a peristaltic pump, a rope pump, a flexible impeller pump, an impulse pump, a velocity pump, a radial flow pump, a mixed-flow pump, an educator-jet pump, a gravity pump, a steam pump, and a valveless pump.

In some cases, the pump is a multi-directional pump. A multi-directional pump can be used to control fluid flow in two or more directions or two more modes of operation (e.g., each mode providing a different pressure or pressure drop). For example, the pump can be a bi-directional pump. The bi-directional pump may supply positive or negative pressure (or pressure drop). The bi-directional pump can control fluid flow in two opposite directions. The pump pressure can be controlled or changed over time while operating the systems or performing the methods described herein. As another example, the pump can operate at multiple modes of operation, such as a first mode in which a first pressure drop is applied and a second mode in which a second pressure drop is applied. The first pressure drop and/or second pressure drop may each yield a positive pressure. As an alternative, the first pressure drop and/or second pressure drop may each yield a negative pressure. As another alternative, the first pressure drop may yield a positive pressure and the second pressure drop may yield a negative pressure.

Figure 12A:
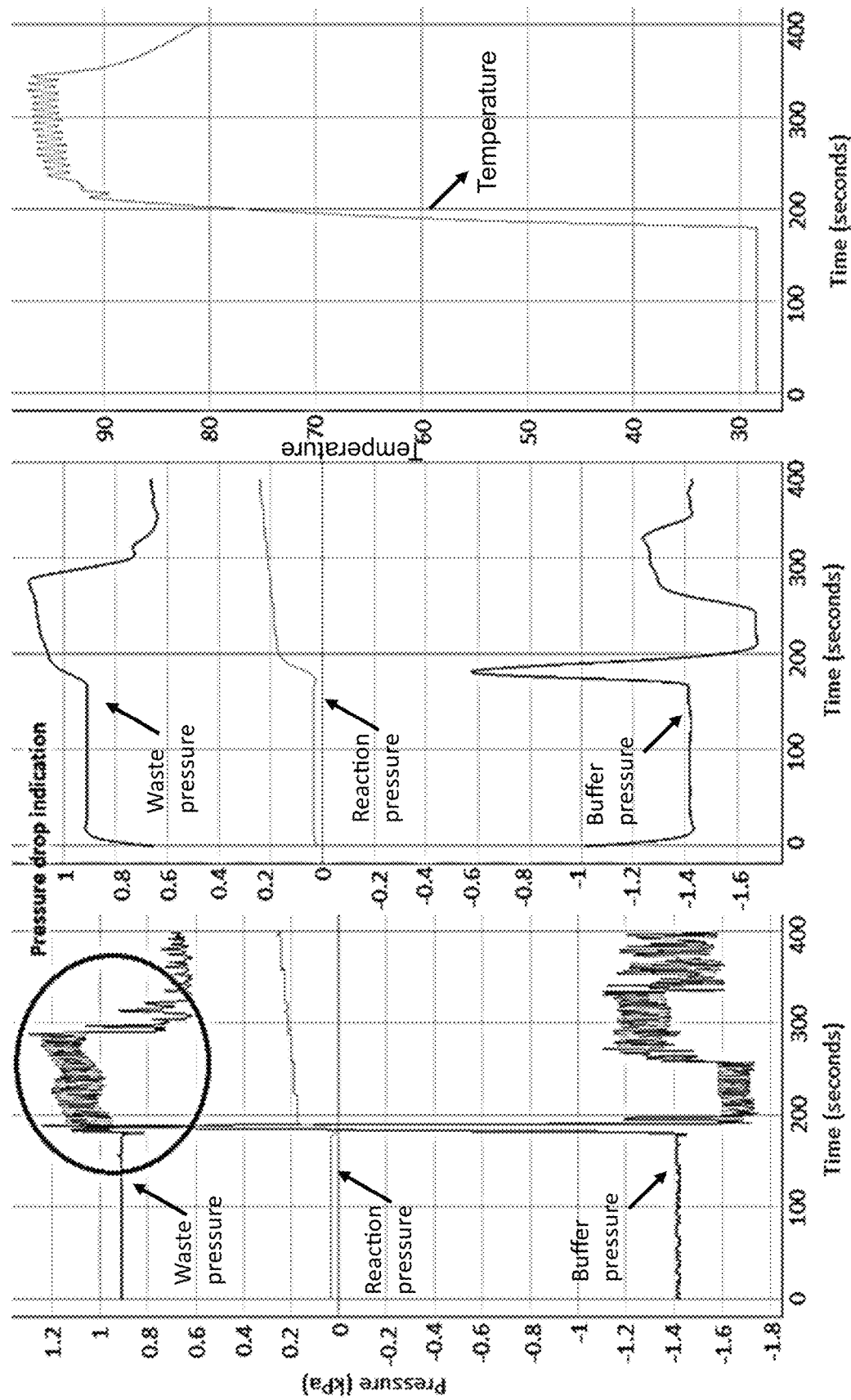
FIG. 12A shows example graphs of buffer pump pressure, waste pump pressure, and reaction pump pressure over time. The circled area indicates pressure drop. The middle panel shows filtered data of pump pressure over time of the left panel. The right panel shows a plot of temperature over time of the heater board of the device as described herein.
Figure 12B:
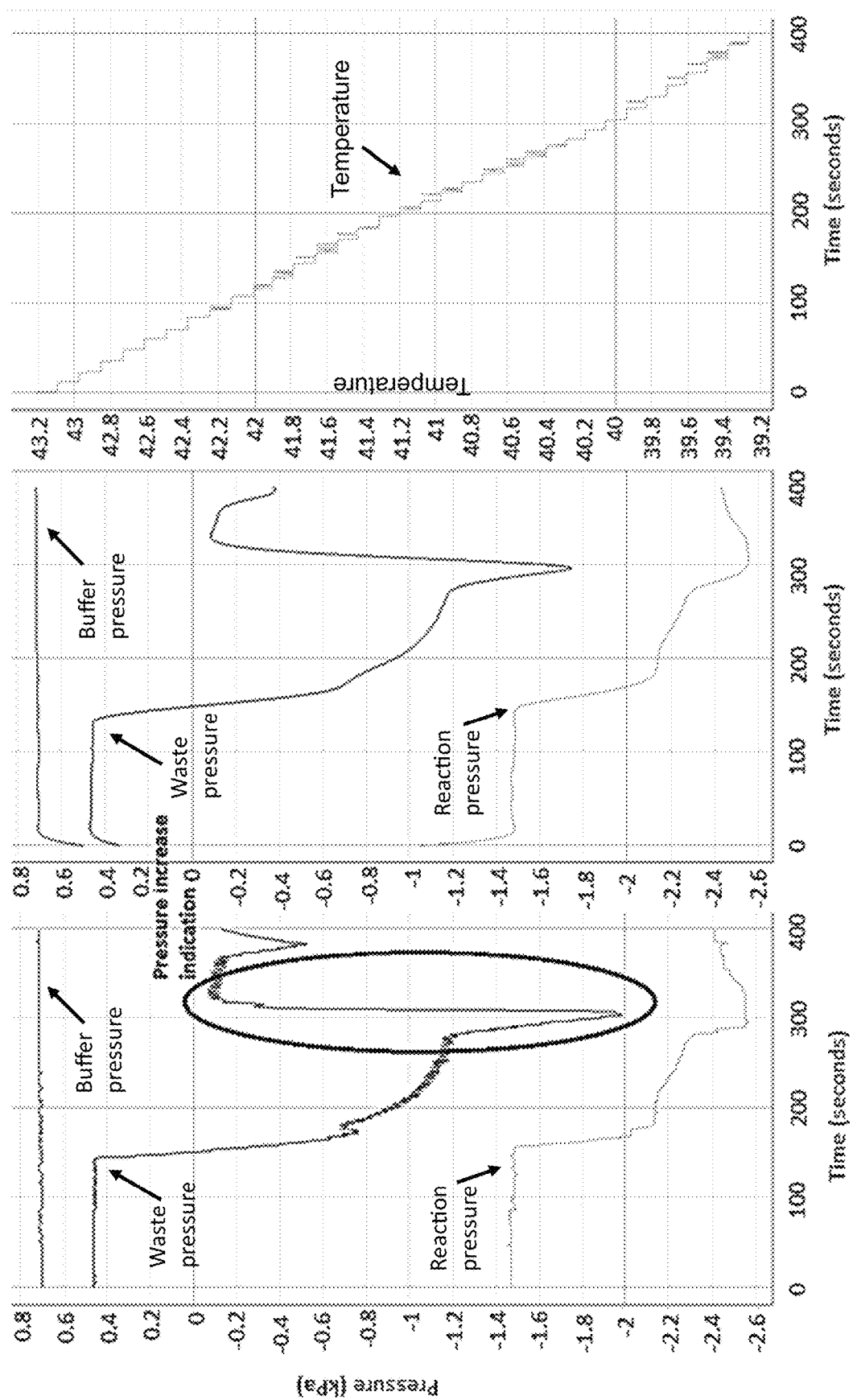
FIG. 12B shows example graphs of buffer pump pressure, waste pump pressure, and reaction pump pressure over time. The circled area indicates pressure increase. The middle panel shows filtered data of pump pressure over time of the left panel. The right panel shows a plot of temperature over time of the heater board of the device as described herein.

A multi-directional pump can supply increased or decreased pressure relative to a reference (e.g., ambient pressure). FIGS. 12A-12B provide example graphs of pump pressure change over time. The systems provided herein can further comprise a pressure sensor included in or connected to the pump. The pressure sensor can measure the pressure of gas or liquid flowing in the conduit coupled to the pump. Such measurement can be used to regulate the pump—for example, with a pressure change, pumping may be terminated. In some cases, the pump pressure sensor monitors pressure of waste pump (e.g., P2 in FIG. 1D). In some cases, the pump pressure sensor monitors pressure of buffer pump (or reagent pump, e.g., P1 in FIG. 1D). In some cases, the pump pressure sensor monitors pressure of reaction pump (or sample pump, e.g., P3 in FIG. 1D).

Pumps of the present disclosure may be configured to supply various pressures or pressure drops. The pressure may be positive pressure or negative pressure. In some examples, a pump (e.g., multi-directional pump) may supply a pressure drop in a range of −50 kPa to 50 kPa, −40 kPa to 40 kPa, −20 kPa to 20 kPa, −10 kPa to 10 kpa, −5 kPa to 5 kPa, or −2 kPa to 2 kPa. The pressure may be greater than or equal to about 0.01 kPa, 0.1 kPa, 1 kPa, 2 kPa, 5 kPa, 10 kPa, 20 kPa, 30 kPa, 40 kPa, 50 kPa, 100 kPa, or greater. The pressure may be less than or equal to about 100 kPa, 50 kPa, 40 kPa, 30 kPa, 20 kPa, 10 kPa, 5 kPa, 2 kPa, 1 kPa, 0.1 kPa, 0.01 kPa, or less.

In some cases, a single pump may be fluidly coupled to (or capable of generating a pressure in) a single conduit. For example, a pump can be disposed along a conduit between a sample chamber and a waste chamber to pump a sample from the sample chamber to the waste chamber. In another example, a pump can be disposed along a conduit downstream of the assay tube to draw a sample from the sample chamber to the assay tube (e.g., the assay tube can be fluidly connected to the sample chamber via an additional conduit. In some cases, a single pump may be fluidly coupled to (or capable of generating a pressure in) multiple conduits simultaneously. For example, a pump can be disposed along a primary conduit, where one end of the primary conduit branches into multiple secondary conduits, each of which is fluidly connected to a chamber.

In another aspect, the present disclosure provides a system comprising a first pump and a second pump in fluid communication with a first fluid flow path. The first pump and the second pump can be multi-directional pumps (e.g., bi-directional pumps). The first pump and the second pump can be configured to subject fluid in the first fluid flow path to flow along a first direction and a second direction. The second direction may be different than the first direction.

For example, the first pump can supply positive pressure to flow a fluid along a first direction. In such instance, the second pump can supply negative pressure to drive the fluid along the first direction. Next, the first pump can supply negative pressure and the second pump can supply positive pressure to flow the fluid along the second direction, which may be opposite to the first direction.

Such system can include at least 1, 2, 3, 4, 5, 6, 7, 8, 9, 10, 20, 30, 40, 50, or more multi-directional pumps. In some cases, the fluid flow path may include valves at least 1, 2, 3, 4, 5, 6, 7, 8, 9, 10, 20, or more valves. As an alternative, the fluid flow path may not include any valves in the fluid flow path.

The fluid flow path may be a channel or conduit. For example, the fluid flow path may be a channel in a polymeric, metallic or composite substrate.

One or more valves may be employed, particularly when a single pump is used to apply a draw pressure to multiple chambers. In the example above, a pump can be disposed along a primary conduit, where one end of the primary conduit branches into multiple secondary conduits, each of which is fluidly connected to a chamber. A valve can be disposed along one or more secondary branches, thereby regulating a pressure applied by a pump on the chamber. A person having skill in the art will appreciate that a variety of valves may be used. Non-limiting examples of valves that may be used include a ball valve, a butterfly valve, a ceramic disc, a clapper valve, a check valve, a choke valve, a diaphragm valve, a gate valve, a globe valve, a knife valve, a needle valve, a pinch valve, a piston valve, a plug valve, a poppet valve, a spool valve, a thermal expansion valve, a pressure reducing valve, a sampling valve, and a safety valve. In some embodiments, the valve can be a one way valve. In some embodiments, the valve can be a two-way valve. In some embodiments, the valve can be a three-way valve. In some embodiments, the valve can be a four-way valve. In some embodiments, a system described herein may not comprise a valve.

Sensors may also be implemented to monitor performance of the sample preparation cartridges and systems. For example, pressure sensors may be used to detect movement of a fluid through one or more conduits of the sample preparation cartridge. In another example, may be used to detect a leak or contamination. In yet another example, optical or electrical sensors may be used to detect a level or amount of fluid within a chamber or conduit. Non-limiting examples of sensors that may be used include a pressure sensor, a moisture sensor, a magnetic sensor, a strain gauge, a force sensor, an inductive sensor, a resistive sensor, a capacitive sensor, an optical sensor, and any combination thereof.

Kits

Provided herein are kits for processing samples. A kit may include one or more sample processing cartridges and/or one or more reagents. The kit may include instructions for processing a sample. The cartridge may be configured to interface with a system of the present disclosure.

The one or more reagents may include lysis buffer, wash buffer, a drying agent, and an elution buffer. For example, the one or more reagents can comprise NP-40 lysis buffer, Radio Immunoprecipitation Assay (RIPA) lysis buffer, sodium dodecyl sulfate (SDS) lysis buffer, Ammonium-Chloride-Potassium (ACK) lysing buffer, volatile chemicals (e.g., acetone and ethanol), EDTA, Tris-HCl, phosphate-buffered saline (PBS), hexamethyldisilazane (HMDS), trichlorotrifluoroethane (Freon 113), tetramethylsilane (TMS), PELDRI II, and water. The one or more reagents can be stable when stored at room temperature. The one or more reagents can be stable for at least one year, at least two years, at least three years, at least four years, at least five years, or more when stored at room temperature.

The one or more reagents may comprise dry agents. The dry agents can be stable when stored at room temperature. The dry agents can be stable for at least one year, at least two years, at least three years, at least four years, at least five years, or more when stored at room temperature The instructions may be in physical (e.g., printed) or electronic form. The instructions may be in print media. As an alternative, the instructions may be accessible by a user on the Internet, such as through a uniform resource locator.

Computer Control Systems

The present disclosure provides computer control systems that are programmed to implement methods of the disclosure. FIG. 9 shows a computer system 901 that is programmed or otherwise configured to process a sample. The computer system 901 can regulate various aspects of the sample preparation device of the present disclosure, such as, for example, activation of a valve or pump to transfer a reagent or sample from one chamber to another. In some aspects, the computer system can regulate which reagents or samples are mixed together, or the rate at which a sample or reagent is transferred from one chamber to another chamber. The computer system 901 can include an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, a current stage of processing of a sample (e.g., a particular step, such as a lysis step, that is being performed). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

EXAMPLES

Example 1. Processing a Water Sample to Detect Waterborne Pathogens Using PCR To detect waterborne bacteria in a water sample, a sample preparation system is initiated, thereby causing a pump to transfer 0.5 mL Tris-EDTA buffer containing RNase A from a reagent chamber into the sample chamber. Once the sample chamber is flooded with Tris buffer, a 1 mL syringe is used to obtain a water sample which is deposited into the sample chamber to mix with the Tris buffer. To maximize the number of bacterial cells exposed to the Tris buffer the bacteria from the water sample are thoroughly suspended in the mixture; a second pump connected to ambient air is used to provide positive pressure into the sample chamber, thereby generating bubbles in the mixture for mixing the sample and the Tris buffer. A valve fluidly connected to a second reagent chamber containing NaOH/SDS (lysis buffer) is opened, and a pump transfers 0.5 mL NaOH/SDS to the sample chamber. Sodium dodecyl sulfate (SDS) solubilizes the phospholipid and protein components of the cell membrane, leading to lysis and release of the cell contents. NaOH denatures the chromosomal and plasmid DNA, as well as proteins. The presence of RNase A ensures that liberated cellular RNA is digested during lysis. The lysis buffer is mixed with the sample and Tris buffer mixture for no more than 5 minutes. A valve fluidly connected to a third reagent chamber containing potassium acetate (neutralizer) is opened, and a pump is used to transfer 0.5 mL potassium acetate to the sample chamber. The high salt concentration causes potassium dodecyl sulfate (KDS) to precipitate, and denatured proteins, chromosomal DNA, and cellular debris are co-precipitated in insoluble salt-detergent complexes. Plasmid DNA, being circular and covalently closed, renatures correctly and remains in solution. A waste pump is used to draw the solution through a filter disposed near the base of the sample chamber, thereby capturing the plasmid DNA in the filter, and transferring a remainder of the solution to the waste chamber. To remove residual neutralizer and/or lysis buffer from the captured DNA, 1 mL acetone is pumped into the sample chamber, and drawn out through the filter to the waste chamber. The acetone wash dilutes and removes impurities in the sample chamber. To remove any residual acetone, a heating pad disposed beneath the sample chamber is activated to heat the sample chamber, thereby vaporizing the residual acetone. A valve fluidly connected to a chamber containing water (elution buffer) is opened, and a pump transfers 0.3 mL water to the sample chamber. The DNA is eluted into the water, and a pump is used to draw 0.1 mL of sample (e.g., water containing the DNA) into each of 3 assay tubes, each assay tube containing a pair of PCR primers for detecting DNA of a bacterial or viral pathogen (e.g., E. coli, Shigella, S. typhi, Hepatitis A virus, Hepatitis E virus)

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for sample processing, comprising:
    a sample chamber comprising a filter configured to capture one or more nucleic acid molecules from a sample in said sample chamber;
    a well fluidly coupled to said sample chamber by a first conduit, said well configured to contain a reagent;
    a fluid flow unit in fluid communication with said first conduit, wherein said fluid flow unit is configured to subject said reagent to flow from said well to said sample chamber;
    an assay tube;
    a cap removably coupled to said assay tube, wherein at least a portion of said cap extends into said assay tube to provide a maximum working volume within said assay tube, wherein said assay tube is in fluid communication with said sample chamber via a second conduit extending through said cap, wherein said cap comprises a self-sealable filter positioned towards an end of an additional conduit extending through said cap, wherein said self-sealable filter is configured to prevent a liquid from said assay tube from entering into said second conduit and said additional conduit under application of a vacuum to said additional conduit when said self-sealable filter comes in contact with said liquid in said assay tube; and
    a controller coupled to said fluid flow unit, wherein said controller is configured to receive instructions from a mobile electronic device for processing of said sample, which instructions, when received by said controller from said mobile electronic device, cause said controller to (i) direct said fluid flow unit to subject said reagent to flow from said well along said first conduit to said sample chamber, to provide a solution comprising said reagent and said one or more nucleic acid molecules in said sample chamber, and (ii) direct said fluid flow unit to subject said solution to flow from said sample chamber along said second conduit to said assay tube, such that said assay tube receives at least a portion of said solution.

2. The system of claim 1, further comprising a second fluid flow unit fluidly coupled to and disposed downstream of said assay tube.

3. The system of claim 1, further comprising a waste chamber fluidly coupled to said sample chamber by a third conduit.

4. The system of claim 3, further comprising a third fluid flow unit disposed along said third conduit between said waste chamber and said sample chamber.

5. The system of claim 1, further comprising a valve disposed along said first conduit between said well and said sample chamber.

6. The system of claim 1, wherein said cap comprises a molecular sieve.

7. The system of claim 1, wherein said assay tube comprises one or more pairs of primers for performing an assay to detect a target nucleic acid molecule.

8. The system of claim 1, further comprising a heater in thermal communication with said sample chamber, wherein said heater is configured to subject a sample in said assay tube to heating.

9. The system of claim 8, wherein said heater is configured to subject said sample to heating as part of one or more heating and cooling cycles.

10. The system of claim 1, wherein said fluid flow unit is a pump or a compressor.

11. The system of claim 1, wherein said fluid flow unit comprises one or more pumps.

12. The system of claim 11, wherein said one or more pumps include a first pump and a second pump, wherein said first pump is configured to subject said reagent to flow from said well to said sample chamber, and wherein said second pump is configured to subject said solution to flow from said sample chamber to said assay tube.

13. The system of claim 1, wherein said controller is configured to come in wireless communication with said mobile electronic device.

14. The system of claim 1, wherein said fluid flow unit comprises or is coupled to a pressure sensor.

15. The system of claim 1, wherein said portion of said cap has a thickness configured to affect said maximum working volume.

16. A method for sample processing, comprising:
    (a) activating a system comprising:
        (i) a sample chamber comprising a filter configured to capture one or more nucleic acid molecules from a sample in said sample chamber;
        (ii) a well fluidly coupled to said sample chamber by a first conduit, wherein said well is configured to contain a reagent;
        (iii) a fluid flow unit in fluid communication with said first conduit, wherein said fluid flow unit is configured to subject said reagent to flow from said well to said sample chamber;
        (iv) an assay tube;
        (v) a cap removably coupled to said assay tube, wherein at least a portion of said cap extends into said assay tube to provide a maximum working volume within said assay tube, wherein said assay tube is in fluid communication with said sample chamber via a second conduit extending through said cap, wherein said cap comprises a self-sealable filter positioned towards an end of an additional conduit extending through said cap, wherein said self-sealable filter is configured to prevent a liquid from said assay tube from entering into said second conduit and said additional conduit under application of a vacuum to said additional conduit when said self-sealable filter comes in contact with said liquid in said assay tube; and
        (vi) a controller coupled to said fluid flow unit, wherein said controller is configured to receive instructions from said mobile electronic device for processing of said sample;
    (b) using said controller to receive said instructions from said mobile electronic device; and
    (c) in accordance with said instructions, using said controller to (i) direct said fluid flow unit to subject said reagent to flow from said well along said first conduit to said sample chamber, to provide a solution comprising said reagent and said one or more nucleic acid molecules in said sample chamber, and (ii) direct said fluid flow unit to subject said solution to flow from said sample chamber along said second conduit to said assay tube, such that said assay tube receives at least a portion of said solution.

17. The method of claim 16, wherein said system further comprises at least one heating unit, wherein said at least one heating unit is in thermal communication with said assay tube, and wherein in accordance with said instructions, said controller directs said at least one heating unit to subject said solution to heating.

18. The method of claim 17, wherein said controller directs said at least one heating unit to subject said solution to one or more heating and cooling cycles.

19. The method of claim 16, wherein in (b), said controller is configured to come in wireless communication with said mobile electronic device.

* * * * *